US012741943B2

(12) United States Patent
Buschmann et al.

(10) Patent No.: US 12,741,943 B2
(45) Date of Patent: Sep. 22, 2026

(54) SODIUM 2-[(4S)-8-FLUORO-2-[4-(3-METHOXYPHENYL)PIPERAZIN-1-Y1]-3-[2-METHOXY-5-(TRIFLUOROMETHYL) PHENYL]-4H-QUINAZOLIN-4-YL]ACETATE MONOHYDRATE, ITS PREPARATION AND USE

(71) Applicant: AIC246 AG & CO. KG, Wuppertal (DE)

(72) Inventors: Helmut Buschmann, Aachen (DE); Thomas Goldner, Velbert (DE); Jordi Carles Ceron Bertran, La Pobla de Montornes (ES)

(73) Assignee: AIC246 AG & CO. KG, Wuppertal (DE)

( * ) Notice: Subject to any disclaimer, the term of this patent is extended or adjusted under 35 U.S.C. 154(b) by 944 days.

(21) Appl. No.: 17/802,815

(22) PCT Filed: Mar. 1, 2021

(86) PCT No.: PCT/EP2021/055065
§ 371 (c)(1),
(2) Date: Aug. 26, 2022

(87) PCT Pub. No.: WO2021/170879
PCT Pub. Date: Sep. 2, 2021

(65) Prior Publication Data

US 2023/0219900 A1 Jul. 13, 2023

(30) Foreign Application Priority Data

Feb. 27, 2020 (EP) .................................... 20159709

(51) Int. Cl.
*C07D 239/84* (2006.01)
*A61P 31/22* (2006.01)

(52) U.S. Cl.
CPC ............ *C07D 239/84* (2013.01); *A61P 31/22* (2018.01); *C07B 2200/13* (2013.01)

(58) Field of Classification Search
CPC .................................................... C07D 239/84
See application file for complete search history.

(56) References Cited

U.S. PATENT DOCUMENTS

| | | | |
|---|---|---|---|
| 8,372,972 | B2 | 2/2013 | Kaethe et al. |
| 8,816,075 | B2 | 8/2014 | Goossen et al. |
| 9,637,459 | B2 | 5/2017 | Grunenberg et al. |
| 2007/0191387 | A1 | 8/2007 | Wunberg et al. |
| 2015/0038514 | A1 | 2/2015 | Grunenberg et al. |
| 2023/0095980 | A1 | 3/2023 | Buschmann et al. |
| 2023/0138444 | A1 | 5/2023 | Buschmann et al. |
| 2023/0150950 | A1 | 5/2023 | Buschmann et al. |
| 2023/0219899 | A1 | 7/2023 | Buschmann et al. |

FOREIGN PATENT DOCUMENTS

| | | | |
|---|---|---|---|
| CL | 2022002291 | A1 | 2/2023 |
| CL | 2022002292 | A1 | 2/2023 |
| CL | 2022002293 | A1 | 2/2023 |
| CL | 2022002294 | A1 | 2/2023 |
| CN | 1784390 | A | 6/2006 |
| CN | 104144917 | A | 11/2014 |
| DE | 10319612 | A1 | 11/2004 |
| JP | 2006525249 | A | 11/2006 |
| JP | 2015508802 | A | 3/2015 |
| WO | 2004096778 | A1 | 11/2004 |
| WO | 2006133822 | A1 | 12/2006 |
| WO | 2013127971 | A1 | 9/2013 |
| WO | 2021170879 | A1 | 9/2021 |

OTHER PUBLICATIONS

Britain et al: "Polymorphism in Pharmaceutical Solids passage", Polymorphism in Pharmaceutical Solids, XX, XX, Jan. 1, 1999 (Jan. 1, 1999), pp. 235-238, XP002278123, ISBN: 978-0-8247-0237-9.
International Search Report PCT/EP2021/055065 dated Mar. 30, 2021 (pp. 1-3) and written opinion (pp. 1-6).
Search report in corresponding EP appl. 20159709 dated Jun. 16, 2020 (pp. 1-8).

*Primary Examiner* — Brian E McDowell
(74) *Attorney, Agent, or Firm* — Millen, White, Zelano & Branigan, P.C.; Brion P. Heaney

(57) ABSTRACT

The compound 3,4-dihydroquinazoline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate of formula (I)

(I)

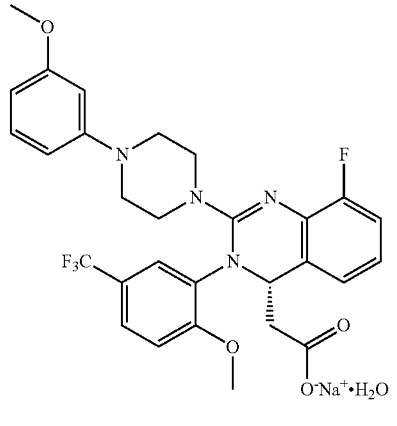

is particularly useful for treatment and prevention of diseases associated with members of the herpes viridae group, including cytomegalovirus (CMV), particularly human cytomegalovirus (HCMV). The compound can be prepared from a suspension of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in diisopropylether, or from a solution of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in methylene chloride.

26 Claims, 9 Drawing Sheets

Thermogravimetric Analysis

Differential scanning calorimetric study

Figure 6
Fig. 6A
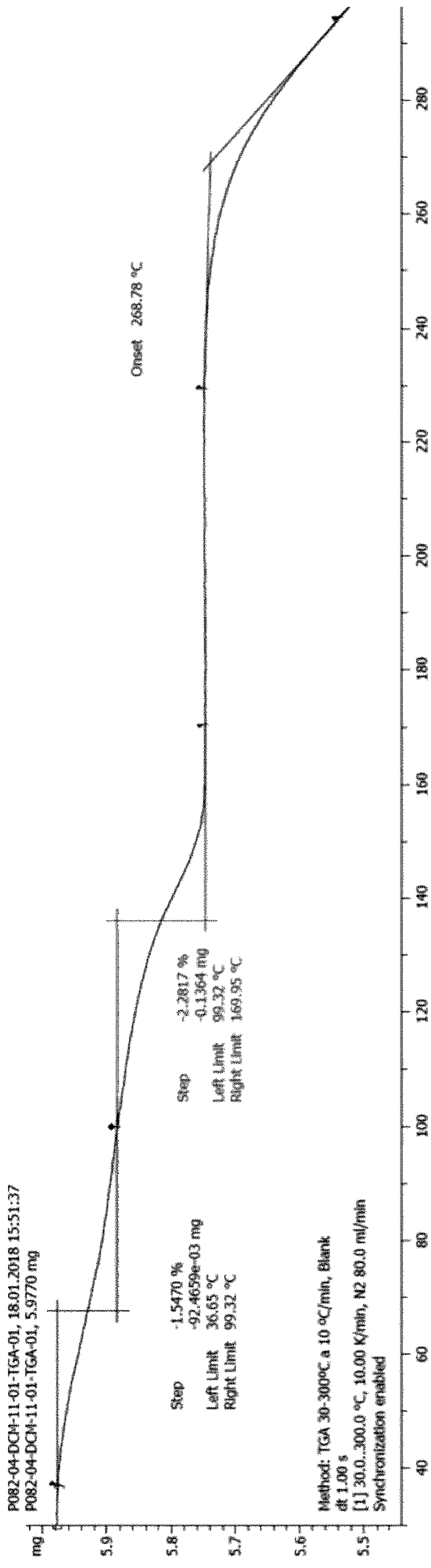
Fig. 6B
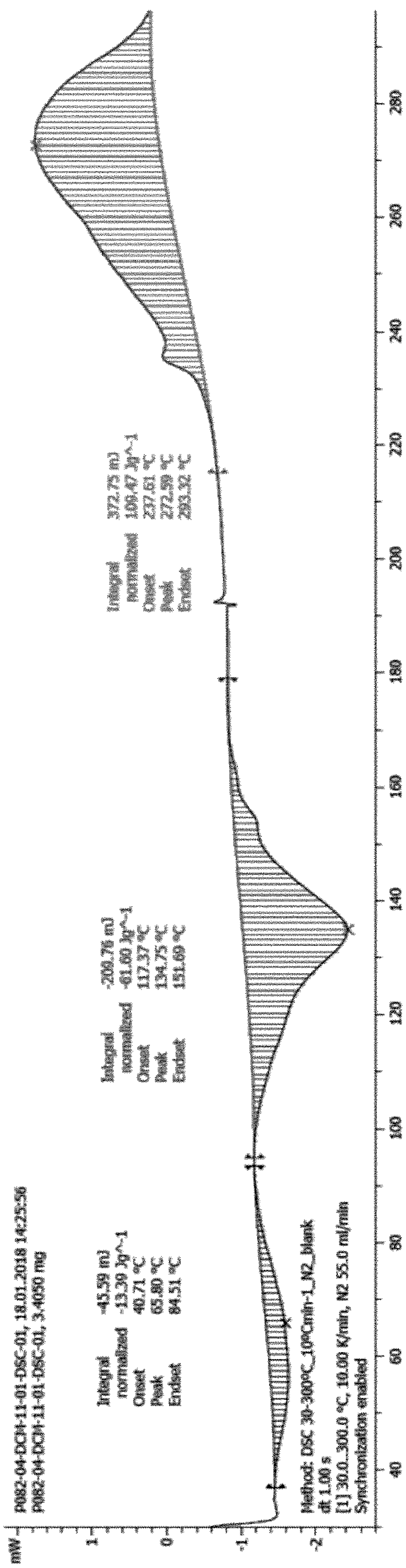

Letermovir sodium monohydrate

Letermovir sodium mixed solvate

SODIUM 2-[(4S)-8-FLUORO-2-[4-(3-METHOXYPHENYL)PIPERAZIN-1-Y1]-3-[2-METHOXY-5-(TRIFLUOROMETHYL) PHENYL]-4H-QUINAZOLIN-4-YL]ACETATE MONOHYDRATE, ITS PREPARATION AND USE

The present invention relates to the novel 3,4-dihydroquinazoline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate, as well as pharmaceutical compositions containing said 3,4-dihydroquinazoline. Said compound is particularly useful for treatment and/or prevention of diseases associated with cytomegalovirus (CMV), particularly human cytomegalovirus (HCMV).

BACKGROUND OF THE INVENTION

Cytomegalovirus (CMV) is a common opportunistic infection that causes significant morbidity and preventable mortality after solid-organ and allogeneic hematopoietic stem cell transplantation.

(S)-(+)-{8-fluoro-2-[4-(3-methoxyphenyl)piperazine-1-yl]-3-[2-methoxy-5-trifluoro-methyl)phenyl]-3,4-dihydroquinazoline-4-yl}acetic acid or 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid is known and herein after referred to as letermovir.

Letermovir is known as a highly active drug for addressing HCMV infection and extensively described in Lischka et al., *In Vitro and In Vivo Activities of the Novel Anticytomegalovirus Compound Letermovir*. Antimicrob. Agents Chemother. 2010, 54: p. 1290-1297, and Kaul et al., *First report of successful treatment of multidrug-resistant cytomegalovirus disease with the novel anti-CMV compound Letermovir*. Am. J. Transplant. 2011, 11:1079-1084; as well as Marschall et al, *In Vitro Evaluation of the Activities of the Novel Anticytomegalovirus Compound Letermovir against Herpesviruses and Other Human Pathogenic Viruses*. Antimicrob. Agents Chemother. 2012, 56:1135-1137. HCMV is a species of virus that belongs to the viral family known as Herpesviridae or herpes viruses. It is typically abbreviated as HCMV and is alternatively known as human herpesvirus-5 (HHV-5). Within Herpesviridae, HCMV belongs to the Betaherpesvirinae subfamily, which also includes cytomegaloviruses from other mammals.

The synthesis of letermovir is disclosed in US 2007/0191387 A1, as well as in WO 2006/133822 and WO 2004/096778.

Salts of letermovir are described in International Publication No. WO 2013/127971. Particularly, some solvates of sodium and calcium salts of letermovir have been prepared in crystalline and amorphous form. In case of the sodium salt of letermovir, mixed alcohol water solvates, such as methanol or ethanol hydrates were obtained (example 1 of WO 2013127971 A1), which can be converted to crystalline letermovir sodium trihydrate (example 2 of WO 2013127971 A1).

There remains a need, however, for a stable crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate form, which does not contain any residual organic solvents and which can be prepared in high yields in a reproducible and scalable process and remains stable in storage over a long period of time.

In order for it to be reasonably possible to use the salts for the development of drugs, the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate form must also remain stable in storage over a long period of time. Finally, the crystalline compound must also be readily soluble in an aqueous medium and particularly at physiological pH.

DESCRIPTION OF THE INVENTION

The first aspect of the present invention relates to a crystalline monohydrate of sodium letermovir of the following formula (I):

(I)

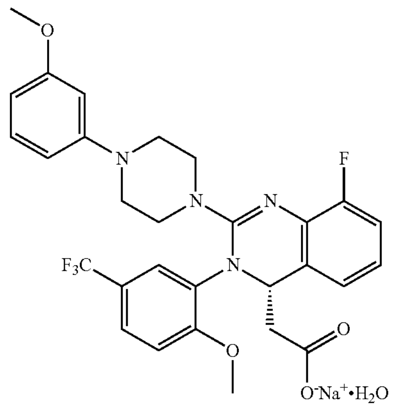

The crystalline monohydrate of sodium letermovir can be easily prepared in high yields from a slurry of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropyl ether and from a solution of known sodium letermovir or a solvate thereof in methylene chloride. Alternatively, the crystalline monohydrate of sodium letermovir can be prepared from a solution of letermovir free base in a mixture of a C1-C6-dialkyl ether and/or a C5-C9-alkane and/or a C5-C9-cycloalkane and acetone, in particular in a mixture of diisopropyl ether and acetone.

It has further been discovered that sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate is readily soluble and also exhibits good storage stability in an aqueous medium, in particular at physiological pH.

Also, the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate does not contain any toxic solvent residuals, thereby rendering said compound particularly useful for the production of pharmaceutical compositions for use in methods of treatment and/or prevention of diseases associated and/or caused by cytomegalovirus (CMV), particularly human cytomegalovirus (HCMV).

Furthermore, the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate which is obtained according to the invention exhibits a high degree of purity.

Sodium 2-[(4S)-8-fluoro-2-[4-(3-methoxyphenyl)piperazin-1-yl]-3-[2-methoxy-5-(trifluoro-methyl)phenyl]-4H- quinazolin-4-yl]acetate monohydrate can be prepared from any monosodium salt of letermovir, or alternatively, from letermovir free base.

Therefore, a further aspect of the present invention is directed to a method of preparation of sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate of formula (I)

(I)

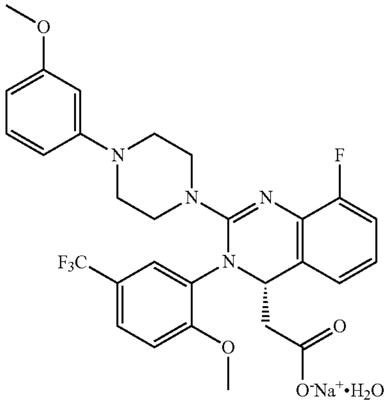

comprising the steps:

A-1) providing a suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropyl ether, B-1) stirring the suspension obtained in step A-1 for at least 10 hours at a temperature in the range of from 40 °C to 60 °C; and C-1) filtering the suspension to obtain sodium 2-[(4S)-8-fluoro-2-[4-(3-methoxy-phenyl)piperazin-1-yl]-3-[2-methoxy-5-(trifluoromethyl)phenyl]-4H-quinazolin-4-yl]acetate monohydrate as a solid, or, alternatively to steps A-1, B-1 and C-1:

A-2) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, B-2) stirring the solution obtained in step A-2 at a temperature of from 40 °C to 60 °C for at least 30 minutes; and C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

Alternatively, the method of preparation of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate monohydrate of formula (I) according to the present invention comprises the steps:

A-3) Providing a solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid in a first solvent, wherein said first solvent comprises at least one C1-C6-dialkyl ether and/or at least one C5-C9-alkane and/or at least one C5-C9-cycloalkane and acetone;

B-3) Adding sodium hydroxide to the solution of step A-3 to provide a first mixture;

C-3) Stirring said first mixture obtained in step B-3 at a temperature in the range of from 25 °C to 80 °C for at least 30 minutes;

D-3) Cooling said first mixture to a temperature in the range of from 0 °C to 30 °C and stirring said first mixture at said temperature for at least 30 minutes;

E-3) Optionally, concentrating said first mixture by evaporation of said first solvent;

F-3) Optionally, stirring said first mixture at a temperature in the range of from 0 °C to 30 °C for at least 10 minutes;

G-3) Contacting said first mixture with a second solvent comprising at least one C1-C6-dialkyl ether and/or at least one C5-C9-alkane and/or at least one C5-C9-cycloalkane to provide a second mixture;

H-3) Stirring said second mixture at a temperature in the range of from 0 °C to 30 °C for at least 1 hour;

I-3) Removing said second solvent to provide a solid.

The method of the present invention has the following technical advantages:

The monosodium letermovir monohydrate can be prepared from any monosodium letermovir salt;

The process has a relatively short reaction time (ca 15 hours);

The process affords directly the letermovir sodium monohydrate (no other transition forms) without any toxic solvent residuals;

The process is reproducible and scalable.

Another aspect of the present invention is the provision of a pharmaceutical composition comprising said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate.

Again another aspect of the present invention is the use of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate or pharmaceutical compositions comprising said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate for the preparation of a medicament for the treatment and/or prevention of diseases, in particular of virus infections, preferably human cytomegalovirus (HCMV) infections or infections with another member of the herpes viridae group.

Again another aspect of the present invention is a method for the treatment and/or prevention of virus infections, preferably human cytomegalovirus (HCMV) infections or infections with another member of the herpes viridae group, in a subject in need thereof by administering said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate or pharmaceutical compositions comprising said crystalline sodium 2-[(4S)-8-fluoro-2-[4-(3-methoxyphenyl)-piperazin-1-yl]-3-[2-methoxy-5-(trifluoromethyl)phenyl]-4H-quinazolin-4-yl] acetate monohydrate.

DETAILED DESCRIPTION

It is noted that the term "comprising" also encompasses the meaning "consisting of", e.g., a group of members comprising said members also encompasses a group of members consisting only of these members.

The term "room temperature" as used herein, is synonymous to the term "standard room temperature" and refers to a temperature in the range of from 19 °C to 26 °C. For example, "cooling down a suspension to room temperature" means "cooling down a suspension to a temperature in the range of from 19 °C to 26 °C".

As used herein, the term "crystal" refers to any three-dimensional ordered array of molecules that diffracts X-rays.

As used herein, the term "unit cell" refers to a basic parallelepiped shaped block. The entire volume of crystal may be constructed by regular assembly of such blocks. Each unit cell comprises a complete representation of the unit of pattern, the repetition of which builds up the crystal.

As used herein, the term "space group" refers to the arrangement of symmetry elements of a crystal.

As used herein, the term "asymmetric unit" refers to a minimal set of atomic coordinates that can be used to generate the entire repetition in a crystal.

As used herein, the term "sodium letermovir monohydrate" refers to sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate.

The term "polymorph" refers to a particular crystal form (i.e. structure of crystal lattice) of sodium letermovir monohydrate that can exist in more than one crystal form in the solid state.

As used herein the term "equivalents" is understood to mean "molar equivalents".

As used herein the term "solvent" refers to a liquid or a mixture of liquids which is suitable for dissolving or solvating a component or material described herein.

As used herein the term "contacting" with respect to two materials refers to the addition of a first material to a second material or the addition of a second material to a first material.

As used herein, the term "concentrating" refers to a process of decreasing the volume of a solution without substantially decreasing the quantity of the substance dissolved or suspended therein. The volume of a solution is decreased, for example, by removing a liquid portion of the solution, in particular by substantially evaporating said liquid portion.

As used herein, the term "dialkyl ether" refers to a group of formula R—O—R, wherein each of the R groups is alkyl.

As used herein the term "alkane" refers to a saturated hydrocarbon with straight or branched chain having the number of carbon atoms designated (i.e. C5-C9-alkyl means five to nine carbon atoms). Non-limiting examples include n-pentane, isopentane, n-hexane, n-heptane, n-octane and n-nonane.

As used herein the term "alkyl" by itself or as part of another substituent refers to a radical of alkane having the number of carbon atoms designated (i.e. C1-C6-alkyl means one to six carbon atoms) and includes straight and branched chains. Non-limiting examples include methyl, ethyl, propyl, isopropyl, butyl, isobutyl, tert butyl, pentyl, neopentyl, and hexyl. For the avoidance of doubt where two alkyl moieties are present in a group, the alkyl moieties may be the same or different.

As used herein, the term "cycloalkane" refers to cyclic aliphatic hydrocarbons containing from 1 to 3 rings and having from 3 to 12 ring carbon atoms.

Within the scope of the present invention the terms "obtained by" and "obtainable by" have the same meaning and are used interchangeably.

As used herein the term "treatment" or "treating" is defined as the application or administration of a therapeutic agent i.e., a monohydrate of letermovir sodium salt (alone or in combination with another pharmaceutical agent) to a subject, or application or administration of a therapeutic agent to an isolated tissue or cell line from a subject who has an HCMV infection, a symptom of HCMV infection, or the potential to develop an HCMV infection with the purpose to cure, heal, alleviate, relieve, alter, remedy, ameliorate, improve or affect the HCMV infection, the symptoms of HCMV infection or the potential to develop an HCMV infection. Such treatments may be specifically tailored or modified based on knowledge obtained from the field of pharmacogenomics.

As used herein the term "prevent", "preventing" or "prevention" means no disorder or disease development if none had occurred, or no further disorder or disease development if there had already been development of the disorder or disease. Also considered is the ability of one to prevent some or all of the symptoms associated with the disorder or disease. Prevention of diseases encompasses prophylaxis of diseases.

As used herein the term "subject" refers to a human or a non-human mammal. Non-human mammals include for example livestock and pets such as ovine, bovine, porcine, feline, canine and murine mammals. Preferably the subject is human.

As used herein the term "pharmaceutically acceptable" refers to a material such as a carrier or diluent which does not abrogate the biological activity or properties of the compound and is relatively non-toxic i.e. the material may be administered to a subject without causing undesirable biological effects or interacting in a deleterious manner with any of the components of the composition in which it is contained.

Sodium Letermovir Monohydrate

Surprisingly, the inventors were able to provide a novel sodium letermovir salt, sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of the formula (I) during crystallization experiments of sodium letermovir salts in various solvents. Among the various screened solvents, the monohydrate salt was obtained basically employing the following methodologies:

- slurry in diisopropyl ether, herein referred to as Steps A-1 to D-1
- crystallization in dichloromethane, herein referred to as Steps A-2 to C-2
- crystallization in acetone/diisopropyl ether, herein referred to as Steps A-3 to I-3
- drying/thermal treatment of form A (obtained from dichloromethane), herein referred to as Steps X-1 to X-4
- crystallization by antisolvent addition (THF/diisopropyl ether)

Said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate may be present in different polymorph forms. Polymorphs are different crystalline forms of the same compound which may have substantially different physicochemical properties, such as solubility, stability and bioavailability. Evaluation of polymorphism of a drug substance plays a crucial role in formulation study because polymorphism may impact drug behavior. For example, rate of dissolution of drug substance impacts the bioavailability of finished products. The solubility, in turn, is dependent on the polymorphic nature of the drug substance. Different polymorphs may have different solubilities and hence the corresponding drug products may have different bioavailabilities.

Different methods for examination of polymorphs can be used. Such methods include microscopy, IR-spectroscopy, Raman spectroscopy, Solid-state NMR, TGA, DSC, XRPD, PDF and other techniques. A combination of different techniques can be applied. In particular, PXRD is a powerful technique for examination of polymorphs. X-rays are reflected from crystals only when the angle between the beam and the planes in the crystal satisfies the Bragg condition. There is an infinite number of possible planes in the crystal. Each molecular repetition gives a unique set of reflections and, therefore, generates a unique pattern, which can be recorded as a spectrum.

However, conventional XRPD analysis yields the average structure of materials, e.g. average positions, displacement parameters and occupancies, and is not able to provide the information about local disorders in the material. For this purpose the Pair Distribution Function (PDF) can be used, which gives the probability of finding an atom at a certain distance from a given atom. The PDF is the Sine-Fourier transform of the total scattering diffraction pattern, which provides the information about average interatomic distances, structural disorders or distortions and average coordination properties. Therefore, the PDF is capable of distinguishing different solid forms of the same compound which are indistinguishable with conventional PXRD analysis. In particular, different amorphous forms which are characterized by different degrees of disorder can be determined by the PDF analysis (Boetker et al. Pharmaceutics 2012, 4, 93-103).

Besides the monohydrate title compound, a different crystalline form of sodium letermovir, which is herein designated as Form A was identified.

The crystalline Form A was obtained by

X-1) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, X-2) stirring the solution for at least 1 hour at a temperature in the range of from room temperature to 40 °C; and X-3) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

The crystalline Form A was characterized by X-ray diffraction (XRD), thermal gravimetric analysis (TGA) and differential scanning calorimetry (DSC) (see FIGS. 5, 6A and 6B). The powder X-ray diffraction pattern shows that crystalline Form A exhibits a medium-high crystallinity.

The X-ray diffraction pattern of said crystalline Form A of sodium letermovir monohydrate comprises 2-theta angle values of 7.4, 10.2, 13.7, 19.6, 23.8 and 25.5 degrees, and said 2-theta angle values have a normal deviation of ±0.1°.

The stability experiments as well as TGA experiments of crystalline Form A revealed that it is not stable under ambient conditions and transforms into the more stable monohydrate Form B within hours.

The transformation of polymorph Form A into Form B can be achieved and accelerated by heating the polymorph Form A at a temperature in the range of from 40 °C to 60 °C in vacuo.

Therefore, the monohydrate Form B can be obtained by a method comprising the following steps X-1) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, X-2) stirring the solution for at least 1 hour at a temperature in the range of from room temperature to 40 °C;

X-3) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid; and X-4) heating the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C to 60 °C in vacuo.

In contrast to the crystalline Form A of sodium letermovir, the monohydrate Form B is thermally stable at high temperatures of considerably above 80 °C as judged by TGA (Decomposition of sodium letermovir monohydrate takes place at 250 °C). Further, Form B of sodium letermovir monohydrate is stable for over 6 months at ambient conditions and does not age at higher temperatures and higher humidity (see Example 09), thereby rendering Form B of sodium letermovir monohydrate particularly suitable for the preparation of stable pharmaceutical compositions.

The obtained Form B of sodium letermovir monohydrate does not contain any toxic solvent residuals as judged by $^1$H NMR spectroscopy (see FIG. 4).

Still more preferably, the X-ray diffraction pattern of said polymorph Form B of sodium letermovir monohydrate comprises 2-theta angle values of 7.0, 9.1, 10.9, 13.3, 14.0, 15.2, 17.4, 18.4 and 24.3 degrees, and said 2-theta angle values have a normal deviation of ±0.1°.

Most preferably, the X-ray diffraction pattern of said polymorph Form B of sodium letermovir monohydrate comprises 2-theta angle values of 7.0, 9.1, 10.9, 12.5, 13.3, 14.0, 15.2, 15.8, 17.4, 18.4, 20.2, 21.1, 22.7, 24.3, 24.9, 26.5, 27.0, 28.4, 29.8 and 30.7 degrees, and said 2-theta angle values have a normal deviation of ±0.1°.

Preparation of Sodium Letermovir Monohydrate

The present invention is further related to a method of preparation of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I)

(I)

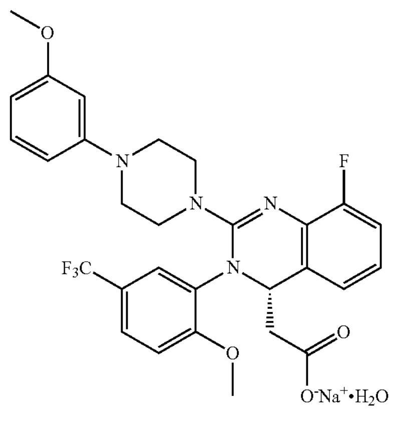

comprising the steps:

A-1) providing a suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropyl ether, B-1) stirring the suspension obtained in step A-1 for at least 10 hours at a temperature in the range of from 40 °C to 60 °C; and C-1) removing the diisopropylether to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid, or, alternatively to steps A1, B-1 and C-1:

A-2) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, B-2) stirring the solution obtained in step A-2 at a temperature of from 40 °C to 60 °C for at least 30 minutes; and C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

In one embodiment, the method is related to the preparation of sodium 2-[(4S)-8-fluoro-2-[4-(3-methoxyphenyl) piperazin-1-yl]-3-[2-methoxy-5-(trifluoromethyl)phenyl]-4H-quinazolin yl]acetate monohydrate of formula (I), the method comprising the steps:

A-1) providing a suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropylether, B-1) stirring the suspension obtained in step A-1 at a temperature in the range of from 40 °C to 60 °C for at least 10 hours, and C-1) removing the diisopropylether to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

In one embodiment, the method is related to the preparation of sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate monohydrate of formula (I), the method comprising the steps:

A-2) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, B-2) stirring the solution obtained in step A-2 at a temperature in the range of from 40 °C to 60 °C for at least 30 minutes; and C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

In one embodiment the method of preparation of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I) further comprises the subsequent step of heating the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C to 60 °C in vacuo.

In one embodiment, the method is related to the preparation of sodium 2-[(4S)-8-fluoro-2-[4-(3-methoxyphenyl) piperazin-1-yl]-3-[2-methoxy-5-(trifluoromethyl)phenyl]-4H-quinazolin yl]acetate monohydrate of formula (I), the method comprising the steps:

A-1) providing a suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropyl ether, B-1) stirring the suspension obtained in step A-1 for at least 10 hours at a temperature in the range of from 40 °C to 60 °C;

C-1) filtering the suspension to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid D-1) optionally, heating the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C to 60 °C in vacuo.

In step A-1 of the herein disclosed methods of preparation of sodium letermovir monohydrate, sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate is suspended in diisopropyl ether at a temperature in the range of from 40 °C to 60 °C. Preferably, the suspension has a temperature in the range of from 42 °C to 58 °C, even more preferably in the range of from 45 °C to 55 °C, even more preferably in the range of from 48 °C to 52 °C and most preferably of 50 °C Preferably, the suspension in step A-1 is provided by suspending amorphous sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a mixed alcohol/water solvate of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate in diisopropyl ether. More preferably, the suspension in step A-1 is provided by suspending amorphous sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate ethanol monohydrate solvate or sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate in diisopropyl ether. Most preferably, the suspension in step A-1 is provided by suspending amorphous sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate in diisopropyl ether.

In one embodiment of the inventive method, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate can be prepared by dissolving letermovir in a 1:1 mixture of ethanol and diisopropyl ether, adding 1.0 mole equivalent of sodium hydroxide, heating the solution to at least 50 °C for at least 3 hours and separating the solid sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate from the reaction mixture.

Preferably in step A-1 of the herein described methods of preparation of sodium letermovir monohydrate, the solid to solvent ratio of sodium 2-[(4S)-8-fluoro-2-[4-(3-methoxyphenyl)-piperazin-1-yl]-3-[2-methoxy-5-(trifluoromethyl) phenyl]-4H-quinazolin-4-yl]acetate to diisopropyl ether is in the range of from 10 g/L to 50 g/L, more preferably in the range of from 20 g/L to 40 g/L and even more preferably in the range of from 25 g/L to 30 g/L. Preferably, the solid to solvent ratio in the suspension is 28 g/L.

In step B-1 of the herein disclosed method of preparation of sodium letermovir monohydrate, the suspension of step A-1 is stirred at a temperature in the range of from 50 °C to 55 °C, preferably at 50 °C for at least 10 hours, preferably for 12 to 18 hours. Preferably, the suspension of step A-1 is stirred at 50 °C for 10 to 24 hours, more preferably for 10 to 20 hours, more preferably for 12 to 18 hours and most preferably for 15 hours. Preferably, the suspension of step A-1 is stirred at 50 °C for 15 hours and then cooled down to room temperature.

Preferably, in step B-1 the suspension of step A-1 is slurried at 50 °C for 12 to 18 hours. More preferably, in step B-1 the suspension of step A-1 is slurried at 50 °C for 15 hours.

In step C-1 of the herein disclosed methods of preparation of sodium letermovir monohydrate, the solvent is removed by filtration, preferably by filtration in vacuo.

In one embodiment, the inventive method further comprises step D-1 after step C-1:

D-1) drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 20 °C to 60 °C in vacuo, preferably for 4 hours or more.

Preferably, in step D-1 of the herein-described method of the preparation of sodium letermovir monohydrate, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 30 °C in vacuo. More preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 40 °C in vacuo. Even more preferably, the sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate monohydrate is heated to 40 °C in vacuo for at least 1 hour. Even more preferably, the sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate monohydrate is heated to 40 °C in vacuo for at least 2 hours. Even more preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate is heated to 40 °C in vacuo for at least 3 hours. Preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 40 °C in vacuo for at least 4 hours.

In one embodiment, the method is related to the preparation of sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate monohydrate of formula (I), wherein the method comprises the steps:

A-2) providing a solution of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in methylene chloride, B-2) stirring the solution at a temperature in the range of from 40 °C to 60 °C for at least 30 minutes; and C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

In a further embodiment, the method is related to the preparation of sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate monohydrate of formula (I), wherein the method comprises the steps:

A-2) providing a solution of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in methylene chloride;

B-2) stirring the solution obtained in step A-2 at a temperature in the range of from 40 °C to 60 °C for at least 30 minutes;

C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid; and D-2) optionally, heating the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C to 60 °C in vacuo.

In step A-2 of the herein disclosed method of preparation of sodium letermovir monohydrate, the solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride can be provided by dissolving a sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate salt or a solvate thereof in methylene chloride. The sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate salt or a solvate can be dissolved in methylene chloride from room temperature to 50 °C. Preferably, the methylene chloride has a temperature in the range of from 20 °C to 50 °C, more preferably in the range of from 25 °C to 50 °C, even more preferably in the range of from 30 °C to 50 °C, even more preferably in the range of from 30 °C to 45 °C, even more preferably in the range of from 35 °C to 45 °C, and most preferably of 40 °C.

Preferably, the solution in step A-2 is provided by dissolving amorphous sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a mixed alcohol/water solvate of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate in methylene chloride. More preferably, the solution in step A-2 is provided by dissolving amorphous sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate ethanol monohydrate solvate sodium 2-[(4S)-8-fluoro-2-[4-(3-methoxyphenyl)piperazin-1-yl]-3-[2-methoxy-5-(trifluoro-methyl)phenyl]-4H-quinazolin-4-yl]acetate trihydrate in methylene chloride. Most preferably, the solution in step A-2 is provided by dissolving sodium 2-[(4S)-8-fluoro-2-[4-(3-methoxyphenyl)piperazin-1-yl]-3-[2-methoxy-5-(trifluoromethyl)phenyl]-4H-quinazolin yl]acetate trihydrate in methylene chloride.

Preferably in step A-2 of the herein described method of preparation of sodium letermovir monohydrate, the concentration of sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate is from 0.5 M to 2 M, more preferably from 0.6 M to 1.9 M and even more preferably from 0.7 M to 1.8 M. Preferably, the solution provided in step A-2 is a concentrated solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate in methylene chloride.

In step B-2 of the herein disclosed method of preparation of sodium letermovir monohydrate, the solution of step A-2 is stirred at a temperature in the range of from 40 °C to 60 °C for at least 30 minutes. Preferably, the solution of step A-2 is stirred at a temperature in the range of from 40 °C to 60 °C for 1 to 4 hours, more preferably for 1 to 3 hours, more preferably for 1 to 2 hours and most preferably for about 1 hour. Preferably, the solution of step A-2 is stirred at a temperature in the range of from 40 °C to 60 °C, preferably at a temperature in the range of from 45 °C to 55 °C, for at least 1 hour and then cooled down to room temperature.

Thus, in one embodiment, the inventive method comprises the steps:

A-2) providing a solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride, B-2) stirring the solution obtained in step A-2 at a temperature in the range of from 40 °C to 60 °C, more preferably at a temperature in the range of from 45 °C to 55 °C for at least 1 hour; and then cooled down to room temperature C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a solid.

In step C-2 of the herein disclosed method of preparation of sodium letermovir monohydrate, the methylene chloride can be removed from the solution of step B-2 with any conventional method suitable for removal of volatile organic compounds. Preferably, the methylene chloride is removed by evaporation. Preferably, the methylene chloride is removed by evaporation at a temperature from room temperature to 40 °C. In one embodiment, the methylene chloride is removed by evaporation at room temperature. In another embodiment, the methylene chloride is removed by evaporation at 40 °C. In another embodiment, the methylene chloride is removed by evaporation at a temperature from room temperature to 40 °C in vacuo. In another embodiment, the methylene chloride is removed by evaporation at room temperature in vacuo. In another embodiment, the methylene chloride is removed by evaporation at 40 °C in vacuo.

In one embodiment, in step C-2 the methylene chloride is removed by lyophilization.

In one embodiment, the inventive method further comprises step D-2 after step C-2:

D-2) drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 30 °C and 60 °C in vacuo, preferably for 4 hours or more.

Preferably, in step D-2 of the herein described method of preparation of sodium letermovir monohydrate, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 40 °C in vacuo. More preferably, the sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate monohydrate is heated to 60 °C in vacuo. Even more preferably, the sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate monohydrate is heated to 60 °C in vacuo for at least 1 hour. Even more preferably, the sodium 2-[(4S)-8-fluoro-2-[4-(3-methoxyphenyl)piperazin-1-yl]-3-[2-methoxy-5-(trifluoromethyl)-phenyl]-4H-quinazolin-4-yl] acetate monohydrate is heated to 60 °C in vacuo for at least 2 hours. Even more preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 60 °C in vacuo for at least 3 hours.

Most preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 60 °C in vacuo for 4 hours.

In one embodiment, the method is related to the preparation of sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate monohydrate of formula (I), the method comprising the steps:

A-3) Providing a solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid in a first solvent, wherein said first solvent comprises at least one C1-C6-dialkyl ether and/or at least one C5-C9-alkane and/or at least one C5-C9-cycloalkane and acetone;

B-3) Adding sodium hydroxide to the solution of step A-3 to provide a first mixture;

C-3) Stirring said first mixture obtained in step B-3 at a temperature in the range of from 25 °C to 80 °C for at least 30 minutes;

D-3) Cooling said first mixture to a temperature in the range of from 0 °C to 30 °C and stirring said first mixture at said temperature for at least 30 minutes;

E-3) Optionally, concentrating said first mixture by evaporation of said first solvent;

F-3) Optionally, stirring said first mixture at a temperature in the range of from 0 °C to 3 0°C for at least 10 minutes;

G-3) Contacting said first mixture with a second solvent comprising at least one C1-C6-dialkyl ether and/or at least one C5-C9-alkane and/or at least one C5-C9-cycloalkane to provide a second mixture;

H-3) Stirring said second mixture at a temperature in the range of from 0 °C to 30 °C for at least 1 hour;

I-3) Removing said second solvent to provide a solid.

In one embodiment the method of preparation of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I) further comprises the subsequent step of drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C to 70 °C, in vacuo.

In one embodiment said C1-C6-dialkyl ether is C1-C4-dialkyl ether, preferably, diisopropyl ether.

In one embodiment the ratio of volumes of C1-C6-dialkyl ether and acetone in step A-3 is in the range of from 3:1 to 1:3. Preferably the ratio of volumes of C1-C6-dialkyl ether and acetone in step A-3 is in the range of from 2:1 to 1:2. More preferably the ratio of volumes of C1-C6-dialkyl ether and acetone in step A-3 is in the range of from 1.5:1 to 1:1.5. Most preferred the ratio of volumes of C1-C6-dialkyl ether and acetone in step A-3 is about 1:1.

In one embodiment 2-[(4S)-8-fluoro-2-[4-(3-methoxyphenyl)piperazin-1-yl]-3-[2-methoxy (trifluoromethyl)phenyl]-4H-quinazolin-4-yl]acetic acid in step A-3 is dissolved at a temperature in the range of from 20 °C to 60 °, preferably in the range of from 40 °C to 60 °C, more preferably in the range of from 45 °C to 55 °C, most preferred at 50 °C.

Preferably in step A-3 of the herein described method, the concentration of 2-[(4S)-8-fluoro-2-[4-(3-methoxyphenyl) piperazin-1-yl]-3-[2-methoxy-5-(trifluoromethyl)phenyl]-4H-quinazolin-4-yl]acetatic acid in said first solvent is from 0.2 M to 0.8 M, more preferably from 0.25 M to 0.6 M, more preferably 0.3 M to 0.5 M, and most preferred from 0.35 M to 0.45 M.

In one embodiment sodium hydroxide in step B-3 is added in the amount of 0.8 to 5 equivalents with respect to letermovir free base. In a preferred embodiment sodium hydroxide in step B-3 is added in the amount of 0.8 to 3 equivalents with respect to letermovir free base. In a more preferred embodiment sodium hydroxide in step B-3 is added in the amount of 0.9 to 2 equivalents with respect to letermovir free base. Most preferred sodium hydroxide in step B-3 is added in the amount of 0.9 to 1 equivalent with respect to letermovir free base.

In one embodiment the mixture in step C-3 is stirred at a temperature in the range of from 25 °C to 80 °C, preferably in the range of from 30 °C to 70 °C, more preferably in the range of from 4°C to 60 °C, even more preferably in the range of from 45 °C to 55 °C, most preferred at 5 C In one embodiment the mixture in step C-3 is stirred at said temperature for at least 30 minutes, more preferably for at least 40 minutes, even more preferably for at least 50 minutes, even more preferably for at least 1 hour, even more preferably for at least 2 hours, in particular for 3 hours. In one embodiment the mixture in step C-3 is stirred at a temperature in the range of from 45 °C to 55 °C for at least 30 minutes. In one embodiment the mixture in step C-3 is stirred at a temperature in the range of from 45 °C to 55 °C for at least 1 hour. In one embodiment the mixture in step C-3 is stirred at a temperature of about 50 °C for at least 2 hours. In one embodiment the mixture in step C-3 is stirred at a temperature of 50 °C for 3 hours.

In one embodiment the mixture in step D-3 is cooled to a temperature in the range of from 0 °C to 30 °C, more preferably in the range of from 10 °C to 30 °, even more preferably in the range of from 20 °C to 30 °C, most preferred to room temperature. In one embodiment the mixture in step D-3 is stirred at said temperature for at least 30 minutes, more preferably for at least 40 minutes, even more preferably for at least 50 minutes, even more preferably for at least 1 hour, even more preferably for at least 8 hours, even more preferably for at least 12 hours, in particular for 16 hours. In one embodiment the mixture in step D-3 is cooled to a temperature in the range of from 20 °C to 30 °C and stirred at said temperature for at least 12 hours. In one embodiment the mixture in step D-3 is cooled to a temperature in the range of from 20 °C to 30 °and stirred at said temperature for 16 hours.

In step E-3 of the herein disclosed method of preparation of sodium letermovir monohydrate, the first solvent can be removed with any conventional method suitable for removal of volatile organic compounds. In one embodiment, said mixture of step D-3 is concentrated by evaporating said first solvent. Preferably, said first solvent is removed by evaporation at a temperature from room temperature to 40 °C. In one embodiment, said first solvent is removed by evaporation at room temperature. In another embodiment, said first solvent is removed by evaporation at 40 °C. In another embodiment, said first solvent is removed by evaporation at a temperature from room temperature to 40 °C in vacuo. In another embodiment, said first solvent is removed by evaporation at room temperature in vacuo. In another embodiment, said first solvent is removed by evaporation at 40 °C in vacuo.

In one embodiment the mixture in step E-3 is concentrated in the way that the volume of said mixture of step D-3 is decreased by at least 10%, more preferably by at least 20%, even more preferably by at least 30%, even more preferably by at least 40%, most preferred by about 50%.

In one embodiment the mixture in step F-3 is stirred at a temperature in the range of from 0 °C to 30 °C, preferably the range of from 10 °C to 30 °C, more preferably in the range of from 20 °C to 30 °C, most preferred to room temperature. In one embodiment the mixture in step F-3 is stirred at said temperature for at least 10 minutes, more preferably for at least 30 minutes, even more preferably for at least 1 hour, in particular for 2 hours.

In one embodiment said first mixture in step G-3 is contacted with a second solvent comprising at least one C1-C6-dialkyl ether and/or at least one C5-C9-alkane and/or at least one C5-C9-cycloalkane. In one embodiment said second solvent comprising at least one C1-C6-dialkyl ether and/or at least one C5-C9-alkane and/or at least one C5-C9-cycloalkane is added to said first mixture in step G-3. In one embodiment said C1-C6-dialkyl ether is C1-C4-dialkyl ether, preferably, diisopropyl ether. Preferably, said second solvent in step G-3 is added in the way that the total volume of the mixture is increased by 1.5 to 5 times, more preferably by 2 to 4 times, even more preferably by 2.5 to 3.5 times, most preferred by about 3 times.

In one embodiment the mixture in step H-3 is stirred at a temperature in the range of from 0 °C to 30 °C, preferably in the range of from 10 °C to 30 °C, more preferably in the range of from 20 °C to 30 °, most preferred at room temperature. In one embodiment the mixture in step H-3 is stirred at said temperature for at least 1 hour, more preferably for at least 2 hours, even more preferably for at least 5 hours, even more preferably for at least 12 hours, in particular for 1 day.

In one embodiment said second solvent in step 1-3 is removed by filtration, preferably by filtration in vacuo.

In one embodiment, the inventive method further comprises step J-3 after step I-3:

J-3) drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 40 °C and 70 °C in vacuo, preferably for 2 hours or more.

Preferably, in step J-3 of the herein described method of preparation of sodium letermovir monohydrate, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 60 °C in vacuo. More preferably, the sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate monohydrate is heated to 60 °C in vacuo for at least 1 hour. Even more preferably, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate is heated to 60 °C in vacuo for at least 2 hours.

The subject-matter of the present invention further relates to crystalline the sodium 2-[(4S)-8-fluoro-2-[4-(3-methoxyphenyl)piperazin-1-yl]-3-[2-methoxy-5-(trifluoromethyl)

phenyl]-4H-quinazolin-4-yl]acetate monohydrate which is obtainable by any embodiment of the method disclosed herein.

Pharmaceutical Composition

Due to its properties and characteristics the sodium letermovir monohydrate according to the invention can be used to produce pharmaceutical compositions that are suitable for use in methods of preventing and/or treating diseases, in particular virus infections.

The following areas of indication can be mentioned, by way of example:

1) Treatment and prevention of HCMV infections in AIDS subjects (retinitis, pneumonitis, gastrointestinal infections).
2) Treatment and prevention of cytomegalovirus infections in bone marrow and solid-organ transplant subjects who often contract life-threatening HCMV pneumonitis or encephalitis, as well as gastrointestinal and systemic HCMV infections.
3) Treatment and prevention of HCMV infections in neonates and infants.
4) Treatment of acute HCMV infection in pregnant women.
5) Treatment of HCMV infection in immune-suppressed subjects suffering from cancer and undergoing cancer therapy.
6) Treatment of HCMV-positive cancer subjects with the aim of reducing HCMV-mediated tumour progression (cf. J. Cinatl, et al., FEMS Microbiology Reviews 2004, 28, 59-77).

The inventive sodium letermovir monohydrate is preferably used to produce pharmaceutical compositions which are suitable for use in prevention and/or treating infections with a representative of the Herpes viridae group, in particular a cytomegalovirus, in particular the human cytomegalovirus. Preferably, the polymorph Form B of sodium letermovir monohydrate is used to produce pharmaceutical compositions which are suitable for use in prevention and/or treating infections with a representative of the Herpes viridae group, in particular a cytomegalovirus, in particular the human cytomegalovirus.

Therefore, in another aspect, the present invention refers to a pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I). Preferably, the pharmaceutical composition comprises further at least one pharmaceutically acceptable carrier, excipient and/or diluent.

Due to its pharmacological properties and characteristics, the crystalline sodium letermovir monohydrate according to the invention, and preferably the polymorph Form B of sodium letermovir monohydrate can be used by themselves and, if needed, also in combination with other active substances, especially antiviral agents.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

Preferably, the pharmaceutical composition comprises the polymorph Form B of sodium letermovir monohydrate.

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain sodium 2-[(4S)-8-fluoro-2-[4-(3-methoxyphenyl)piperazin-1-yl]-3-[2-methoxy-5-(trifluoromethyl)phenyl]-4H-quinazolin yl]acetate monohydrate.

The pharmaceutical compositions according to the present invention containing sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate monohydrate according to the present invention as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the inventive sodium 2-[(4S)-8-fluoro-2-[4-(3-methoxyphenyl)

piperazin-1-yl]-3-[2-methoxy-5-(trifluoromethyl)phenyl]-4H-quinazolin-4-yl]acetate monohydrate of formula (I) as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate monohydrate may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood, which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses, such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances, which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The inventive sodium letermovir monohydrate exhibits an antiviral effect against representatives of the Herpes viridae group (herpes viruses), above all against the cytomegaloviruses (CMV), in particular against the human cytomegalovirus (HCMV). They are thus suitable for use in methods of treating and preventing diseases, especially infections with viruses, in particular the viruses referred to herein and the infectious diseases caused by them. The term "virus infection" is understood here to mean not only an infection with a virus but also a disease caused by infection with a virus.

Thus, another aspect of this invention refers to the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate or a pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate for use in a method of treatment and/or prevention of infectious diseases caused and/or associated by cytomegalovirus, particularly human cytomegalovirus.

Further, the invention relates to the use of the crystalline sodium 2-[(4S)-8-fluoro-2-[4-(3-methoxyphenyl)piperazin-1-yl]-3-[2-methoxy-5-(trifluoromethyl)phenyl]-4H-quinazolin yl]acetate monohydrate or the pharmaceutical composition comprising the crystalline sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate monohydrate for the preparation of a medicament for the treatment and/or prevention of diseases, in particular of virus infections, preferably human cytomegalovirus (HCMV) infections or infections with another member of the herpes viridae group.

Further, the invention provides a method of treating and/or preventing of a disease associated and/or caused by cytomegalovirus (CMV), particularly human cytomegalovirus (HCMV), or infections with another member of the herpes viridae group which comprises administering to said subject a therapeutically effective amount of crystalline sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate monohydrate or or the pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate. Preferably, the method of treating and/or preventing of a disease associated and/or caused by cytomegalovirus (CMV), particularly human cytomegalovirus (HCMV) comprises administering to said subject a therapeutically effective amount of polymorph Form B of crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I).

The term "effective amount" means an amount of compound that, when administered to a subject in need of such treatment, is sufficient to (i) treat or prevent a particular disease, condition, or disorder;
(ii) attenuate, ameliorate, or eliminate one or more symptoms of the particular disease, condition, or disorder; or
(iii) prevent or delay the onset of one or more symptoms of the particular disease, condition, or disorder described herein.

The amount of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I) that will correspond to such an amount will vary depending upon factors such as the particular compound, disease condition and its severity, the identity (e.g., weight) of the subject in need of treatment, but can nevertheless be routinely determined by one skilled in the art.

Abbreviations h hour(s)
DSC differential scanning calorimetry
HPLC high pressure liquid chromatography
min. minutes
NMR nuclear magnetic resonance
PDF pair distribution function
TGA thermogravimetric analysis
XRPD X-ray powder diffraction

DESCRIPTION OF THE FIGURES

FIG. 6 shows A) thermogravimetric analysis and B) differential scanning calorimetric study of crystalline Form A of letermovir sodium.

FIG. 1 of WO 2013127971) and letermovir sodium mixed solvate (above).

Figure 1:
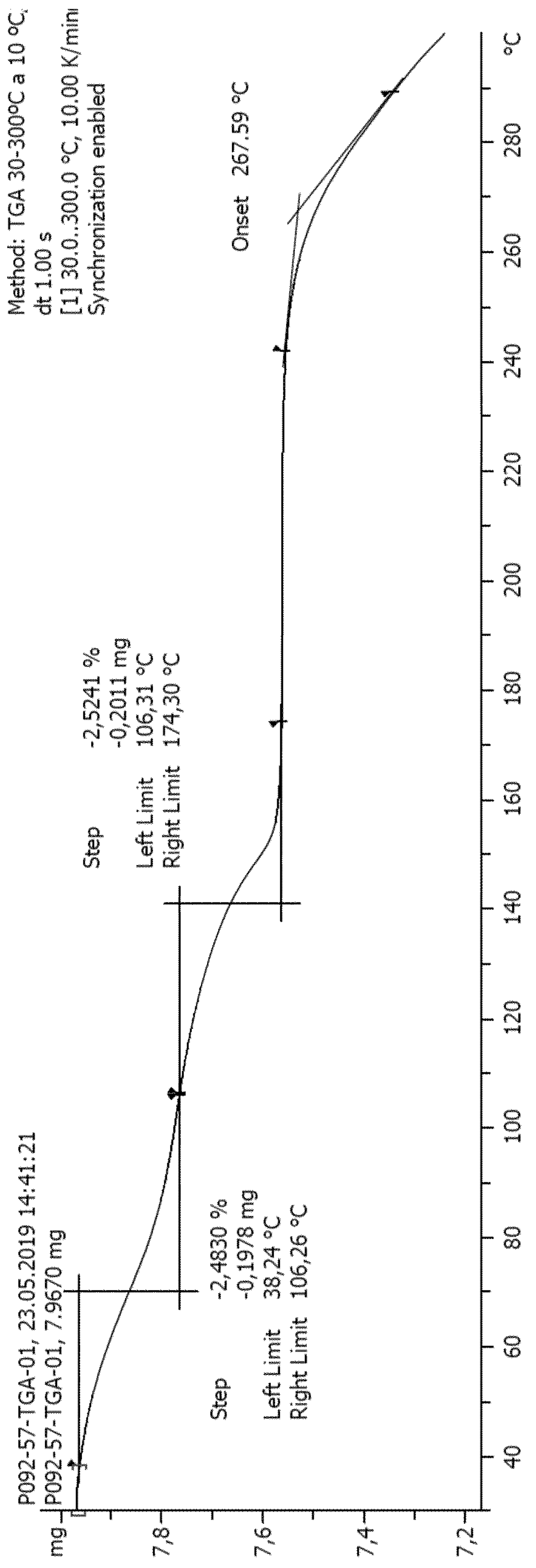
FIG. 1 shows a thermogravimetric analysis of Form B of letermovir sodium monohydrate.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Equipment Used

Powder X-Ray Diffraction analysis (PXRD): Approximately 20 mg of sample were prepared in standard sample holders using two foils of polyacetate. The samples were analysed as received without further manipulation. Powder diffraction patterns were acquired on a D8 Advance Series 2Theta/Theta powder diffraction system using CuKα1-radiation (1.54060 Å) in transmission geometry at room temperature. The system is equipped with a VÅNTEC-1 single photon counting PSD, a Germanium monochromator, a ninety positions autochanger sample stage, fixed divergence slits and a radial soller. The generator intensity for the generation of the X-ray beam is set to 40 mA and 40 kV. Programs used: Data collection with DIFFRAC plus XRD Commander V.2.5.1, and evaluation with EVA V.14.0.0.0 (Bruker-AXS 1996-2007). The patterns were collected in thirty minutes measurements in a range from 4 to 40 °C in 2θ (step size 0.049°).

Proton nuclear magnetic resonance spectroscopy ($^1$H-NMR): Proton nuclear magnetic resonance analyses were recorded in deuterated DMSO (DMSO-$d_6$) in a Bruker Avance 400 Ultrashield NMR spectrometer. Spectra were acquired solving 8-10 mg of sample in 0.7 mL of deuterated solvent.

Differential scanning calorimetry analysis (DSC): DSC analyses were recorded in a Mettler Toledo DSC822 with a 56-point Au—AuPd thermopile FRSS sensor. Approximately 2-3 mg of sample were weighed (using a MX5 Mettler Toledo microbalance) into 40 μL aluminium crucibles with a pinhole lid and heated at 10 and/or 20 °C/min from 30 °C. to 300 °C under nitrogen (50 mL/min). Programs used: Data collection and evaluation with software STARe.

Thermogravimetric analysis (TGA): Thermogravimetric analyses were recorded in a Mettler Toledo TGA/SDTA851 with a balance MT1 type. Approximately 3-4 mg of sample were weighed (using a MX5 Mettler Toledo microbalance) into 40 μL aluminium crucibles with a pinhole lid and heated under nitrogen (10 mL/min) at 10 °C/min from 30 °C to 300 °C. Programs used: Data collection and evaluation with software STARe.

Single Crystal X-ray Diffraction (SCXRD): The measured crystals were selected using a Zeiss stereomicroscope using polarized light and prepared under inert conditions immersed in perfluoropolyether as protecting oil for manipulation. All selected samples corresponded to multi-component crystals. Crystal structure determinations at 100 K were carried out using a Apex DUO Kappa 4-axis goniometer equipped with an APPEX 2 4K CCD area detector, a Microfocus Source E025 luS using $MoK_\alpha$ radiation, Quazar MX multilayer Optics as monochromator and an Oxford Cryosystems low temperature device Cryostream 700 plus (T=100 K). Fullsphere data collection omega and phi scans. Programs used: Data collection APEX II (APEX II version v2009.1-02. Bruker (2007). Bruker AXS Inc., Madison, Wisconsin, USA), data reduction with SAINT (Bruker SAINT version V7.60A. Bruker (2007). Bruker AXS Inc., Madison, Wisconsin, USA) and absorption correction with SADABS (SADABS: V2012/1 Bruker (2001). Bruker AXS Inc., Madison, Wisconsin, USA. Blessing, Acta Cryst. (1995) A51 33-38). Crystal structure solution was achieved with the program SHELXT (SHELXT Crystal Structure Solution Version 2014/4, George M. Sheldrick 2010-2014; Sheldrick, G. M. *Acta Cryst.* 2015 A71, 3-8) and visualized using the program SHELXle (C. B. Huebschle, G. M. Sheldrick & B. Dittrich; J. Appl. Cryst. (2011) 44, 1281-1284). Missing atoms were subsequently located from difference Fourier synthesis and added to the atom list. Least-squares refinement on $F_0^2$ using all measured intensities was carried out using the program SHELXL 2015 (SHELXL Crystal Structure Refinement Version 2014/7, George M. Sheldrick 1993-2014; Sheldrick, G. M. *Acta Cryst.* 2015 C71, 3-8). All non-hydrogen atoms were refined including anisotropic displacement parameters.

Example 01: Preparation of Sodium (S)-{8-fluoro-2-[4-(3-methoxyphenyl)piperazin-1-yl]-3-[2-methoxy-5-(trifluoromethyl)phenyl]-3,4-dihydroquinazoline-4-yl}acetate The title compound was prepared from (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (letermovir) according to the method described in WO 2013127971 A1.

333.1 g of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid are dissolved in 1300 ml of a mixture of ethanol and diisopropyl ether (1:1) in a 2000 ml three-neck flask. 21.9 g (546.84 mmol) of NaOH are added as a solid to the solution. The mixture is heated for 25 min to an inner temperature of 50 °C, and this yields a clear orange-coloured solution. The solution thus obtained is stirred for 3 hours at this temperature, and a thin suspension is formed already after 1 hour. The reaction mixture is then cooled down for 10 hours at a cooling rate of 3 °C/hour to an inner temperature of 20 °C and then stirred for a further 5 hours at this temperature. The total volume of the reaction mixture is reduced under vacuum to approximately 750 mL and the suspension obtained in this way is stirred at 20 °C for 2 hours. Next, 250 mL diisopropyl ether is added over a period of 10 min to the reaction mixture obtained and the mixture is stirred for further 2 hours. The crystalline product which is obtained is vacuumed off by a suction device, washed 2× with—in each case—250 mL diisopropyl ether, and dried in a vacuum drying cabinet for 20 hours at 20 °C and 160 mbar. The crystalline solid obtained in this way is then dried for 10 min at 90 °C in an IR dryer and then again for further 16 hours at 60 °C in the vacuum drying cabinet. In this way a total of 274.4 g (86% of the theoretical yield) of the desired crystalline sodium salt of letermovir ethanol monohydrate is obtained.

TABLE 1

The crystal data and structure refinement for the crystalline of letermovir sodium ethanol monohydrate.

| | | |
|---|---|---|
| Identification code | mo_P07701NOHEOH_0m | |
| Empirical formula | C31 H35 F4 N4 Na O6 | |
| Formula weight | 658.62 | |
| Temperature | 100(2) K | |
| Wavelength | 0.71073 Å | |
| Crystal system | Trigonal | |
| Space group | R3 | |
| Unit cell dimensions | a = 28.4046(16)Å | α = 90° |
| | b = 28.4046(16)Å | β = 90° |
| | c = 10.0751(5)Å | γ = 120° |

TABLE 1-continued

| The crystal data and structure refinement for the crystalline of letermovir sodium ethanol monohydrate. | |
|---|---|
| Volume | 7039.7(9) Å$^3$ |
| Z | 9 |
| Density (calculated) | 1.398 Mg/m$^3$ |
| Absorption coefficient | 0.124 mm$^{-1}$ |
| F(000) | 3996 |
| Crystal size | 0.20 × 0.20 × 0.10 mm$^3$ |
| Theta range for data collection | 2.184 to 36.652°. |
| Index ranges | −4 ≤ h ≤ 20, −40 ≤ k ≤ 28, −12 ≤ 1 ≤ 10 |
| Reflections collected | 13091 |
| Independent reflections | 775.3[R(int) = 0.0182] |
| Completeness to theta = 30.652° | 95.3% |
| Absorption correction | Multi-scan |
| Max. and min. transmission | 0.988 and 0.947 |
| Refinement method | Full-matrix least-squares on F$^2$ |
| Data/restraints/parameters | 7753/133/462 |
| Goodness-of-fit on F$^2$ | 1.029 |
| Final R indices [I > 2sigma(I)] | R1 = 0.0475, wR2 = 0.1192 |
| R indices (all data) | R1 = 0.0531, wR2 = 0.1239 |
| Flack parameter | x = 0.13(15) |
| Largest diff. peak and hole | 0.794 and −0.413 e · Å$^{-3}$ |

Example 02: Alternative Preparation of Sodium (S)-{8-fluoro-2-[4-(3-methoxyphenyl)-piperazin-1-yl]-3-[2-methoxy-5-(trifluoromethyl)phenyl]-3,4-dihydroquinazoline-4-yl}acetate 50 grams of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (letermovir) were dissolved in 200 mL of a 1:1 ethanol/diisopropyl ether mixture. 3.3 grams of sodium hydroxide were added and the solution is heated to 50 °C. The mixture is stirred for 6 hours at this temperature and subsequently cooled down and stirred at room temperature for 60 hours. The obtained suspension is filtered off, affording 24 grams of the crystalline sodium salt of letermovir ethanol monohydrate (80% yield).

Example 03: Preparation of Amorphous Sodium (S)-{8-fluoro-2-[4-(3-methoxy-phenyl)piperazine-1-yl]-3-[2-methoxy-5-(trifluoromethyl)phenyl]-3,4-dihydroquinazoline-4-yl}acetate Crystalline sodium (S)-{8-fluoro-2-[4-(3-methoxyphenyl)piperazin-1-yl]-3-[2-methoxy-5-(trifluoromethyl)phenyl]-3,4-dihydroquinazoline-4-yl}acetate obtained from (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (letermovir) according to the method described in Example 01 or 02 was dried at 120 °C under vacuum for 15 hours. The amorphous title compound was obtained in nearly quantitative yield.

Example 04: Alternative Preparation of Amorphous Sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate 1 gram crystalline sodium (S)-{8-fluoro-2-[4-(3-methoxyphenyl)piperazin-1-yl]-3-[2-methoxy-5-(trifluoromethyl)phenyl]-3,4-dihydroquinazoline-4-yl}acetate obtained from (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (letermovir) according to the method described in Example 01 or 02 was dissolved in 5 mL water. The solution was frozen using liquid nitrogen and lyophilized for 15 hours (−80 °C, 0.03 mBar). The amorphous title compound was obtained in nearly quantitative yield.

Example 05: Preparation of Sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate monohydrate 3.5 grams of amorphous sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Example 03 or 04) were slurried in diisopropyl ether (125 mL) at 50 °C with a gentle stirring (Anchor stirrer, 180 rpm) 15 hours. After that time the solution was filtered off to afford a compact white solid. The obtained solid was dryed in vacuo at 40 °C for 4 hours. The title compound was obtained as a white solid (3.2 g, 89 yield).

Example 06: Alternative preparation of sodium (S)-{8-fluoro-2-[4-(3-methoxyphenyl)-piperazine-1-yl]-3-[2-methoxy-5-(trifluoromethyl)phenyl]-3,4-dihydroquinazoline-4-yl}acetate monohydrate 2 g of amorphous sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Example 03 or 04) were dissolved in tetrahydrofurane (5 mL) at 52 °C. Then, 50 mL of diisopropyl ether (antisolvent) were added using an addition funnel (1-1.5 mL/min) and a precipitate was formed when almost all the diisopropyl ether had been added. Right after the complete addition of the antisolvent the suspension was filtered to afford a compact white solid. The obtained solid was dryed in vacuo at 40 °C for 4 hours. The title compound was obtained as a white solid (0.465 g, 22% yield).

Figure 4:
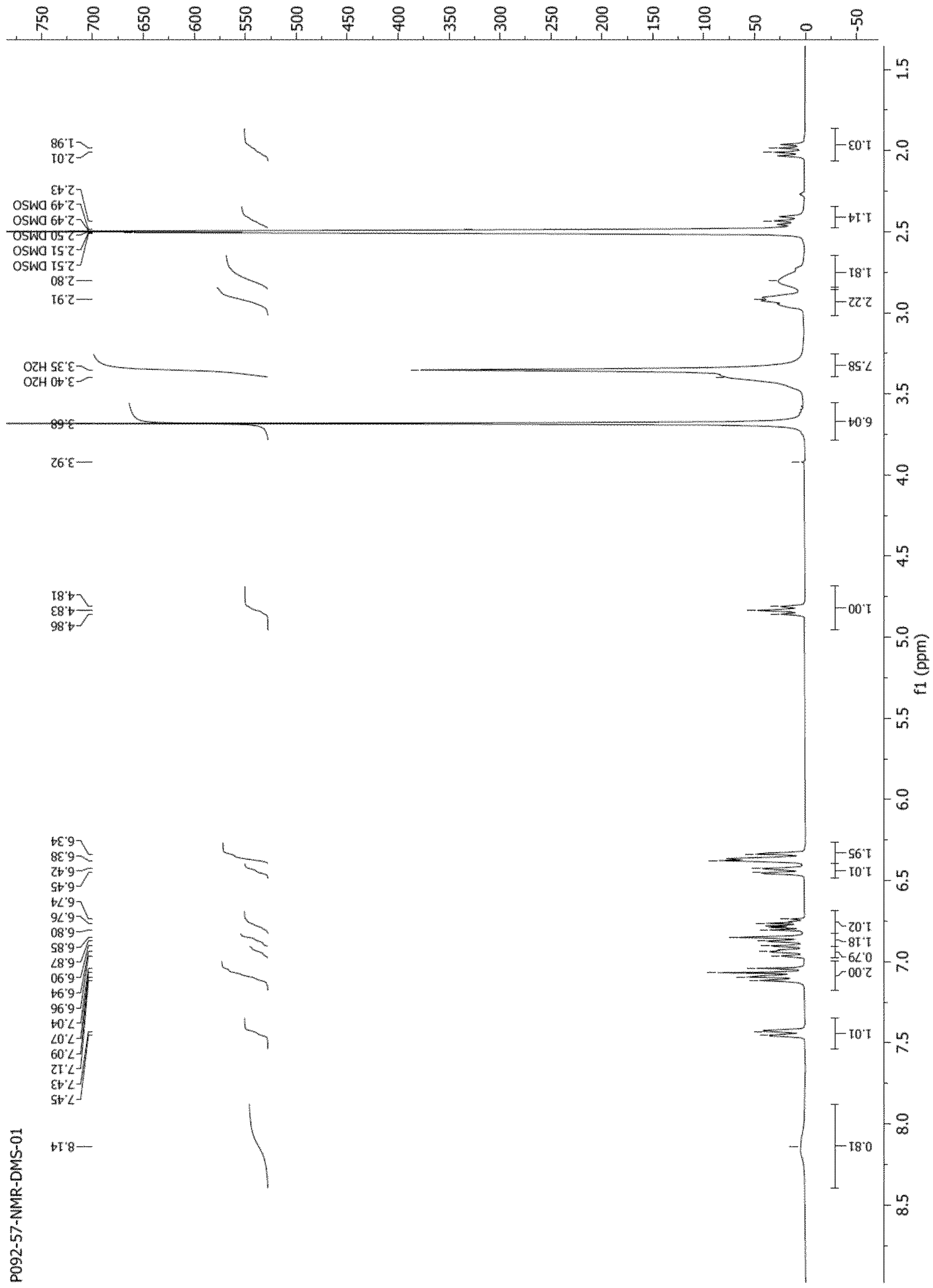
FIG. 4 shows an $^1$H NMR spectrum of letermovir sodium monohydrate in DMSO-$d_6$.

Example 07: Alternative Preparation of Sodium (S)-{8-fluoro-2-[4-(3-methoxyphenyl)-piperazine-1-yl]-3-[2-methoxy-5-(trifluoromethyl)phenyl]-3,4-dihydroquinazoline-4-yl}acetate monohydrate 1 gram of amorphous sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Example 03 or 04) was dissolved in 2.5 mL methylene chloride at 40 °C and stirred for 1 hour at this temperature. Afterwards, the solution was cooled down and the solvent was evaporated at room temperature. The remaining solid was dried in vacuo at 60 °C for 4 hours. The title compound was obtained nearly quantitatively as a white solid. FIG. 4 shows a $^1$H NMR spectrum of the title compound.

Example 08: Alternative Preparation of Sodium (S)-{8-fluoro-2-[4-(3-methoxyphenyl)-piperazine-1-yl]-3-[2-methoxy-5-(trifluoromethyl)phenyl]-3,4-dihydroquinazoline-4-yl}acetate monohydrate 5 grams of crystalline sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Exaple 01 or 02) were dissolved in 5 mL methylene chloride at 45

°C-50 °C. and stirred for 1 hour at this temperature. Afterwards, the solution was cooled down and the solvent was evaporated at room temperature. The remaining solid was dried in vacuo at 60 °C for 4 hours. The title compound was obtained nearly quantitatively as a white solid. FIG. 4 shows a $^{1}$H NMR spectrum of the title compound.

Example 09: Alternative Preparation of Sodium (S)-{8-fluoro-2-[4-(3-methoxyphenyl)-piperazine-1-yl]-3-[2-methoxy-5-(trifluoromethyl)phenyl]-3,4-dihydroquinazoline-4-yl}acetate monohydrate 5 grams of letermovir free base were dissolved in a mixture of acetone and diisopropyl ether (1:1, 19.5 mL). Afterwards, sodium hydroxide was added (0.3285 g, 8.2 mmol) and the obtained mixture was heated to 50 °C and stirred for 3 hours. The mixture was cooled to room temperature and stirred overnight. The volume of the resulting mixture was reduced to a half (evaporation in the rotary evaporator) and the resulting solution was stirred at room temperature for 2 hours. An additional portion of diisopropyl ether (20 mL) was added, and the resulting suspension was stirred at room temperature overnight.

The crystallized solid was filtered off and dried under vacuum at 60 °C for 2 hours, yielding 5.05 g (97%) of letermovir sodium monohydrate salt. FIG. 4 shows a $^{1}$H NMR spectrum of the title compound.

Reference Example 10: Preparation of Sodium (S)-{8-fluoro-2-[4-(3-methoxyphenyl)-piperazine-1-yl]-3-[2-methoxy-5-(trifluoromethyl)phenyl]-3,4-dihydroquinazoline-4-yl}acetate Mixed Solvate (corresponds to the procedures according to Example 1 and 2 of WO 2013127971) 333.1 g of 2-[(4S)-8-fluoro-2-[4-(3-methoxyphenyl)piperazin-1-yl]-3-[2-methoxy-5-(trifluoro-methyl)phenyl]-4H-quinazolin-4-yl]acetic acid were dissolved in 1300 mL of a mixture of ethanol and diisopropyl ether (1:1) in a 2000 mL three-neck flask. 21.9 g (546.84 mmol) of NaOH were added as a solid to the solution. The mixture was heated for 25 min. to an inner temperature of 50 °C, and this yielded a clear orange-coloured solution. The solution thus obtained was stirred for 3 hours at this temperature, and a thin suspension formed already after 1 hour. The reaction mixture was then cooled down for 10 hours at a cooling rate of 3 °C/hour to an inner temperature of 20 °C and then stirred for a further 5 hours at this temperature. The total volume of the reaction mixture was reduced under vacuum to approximately 750 mL and the suspension obtained in this way was stirred at 20 °C for 2 hours. Next, 250 mL diisopropyl ether was added over a period of 10 min to the reaction mixture obtained and the mixture was stirred for further 2 hours. The crystalline product which was obtained was vacuumed off by a suction device, washed 2× within each case 250 mL diisopropyl ether, and dried in a vacuum drying cabinet for 20 hours at 20 °C and 160 mbar. The crystalline solid obtained in this way was then dried for 10 min. at 90 °C in an IR dryer and then again for further 16 hours at 60 °C in the vacuum drying cabinet. In this way a total of 274.4 g (86% of the theoretical yield) of the desired crystalline sodium salt was obtained.

About 300 mg of the obtained sodium salt of 2-[(4S)-8-fluoro-2-[4-(3-methoxyphenyl)piperazin-1-yl]-3-[2-methoxy-5-(trifluoromethyl)phenyl]-4H-quinazolin-4-yl] acetic were suspended in 1 mL ethanol (containing 4% water) and shaken for a week at 25 °C. The crystalline obtained was filtered off and the residue was dried at room temperature and ambient humidity, yielding letermovir sodium mixed ethanol solvate.

Figure 9:
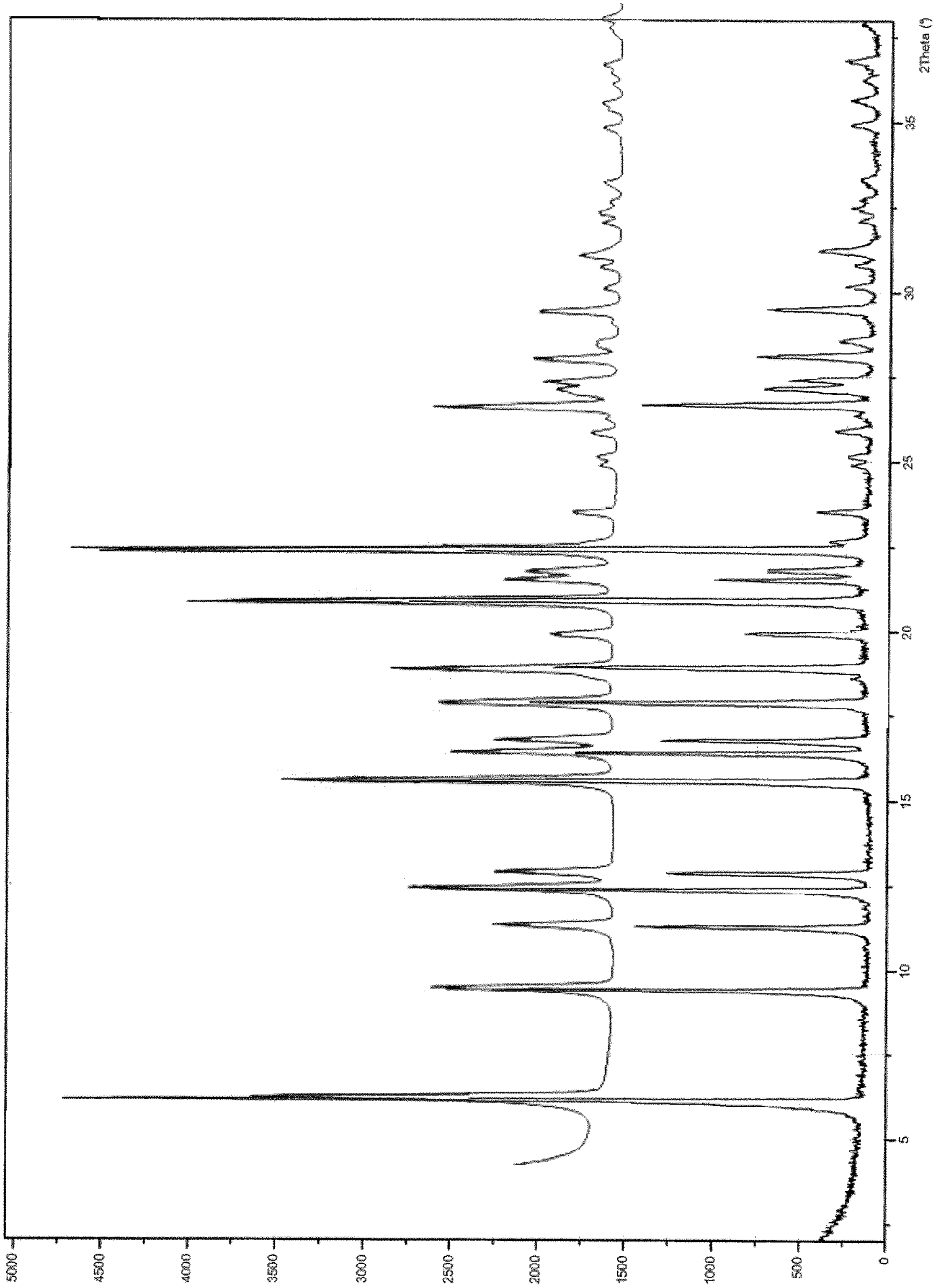
FIG. 9 shows a comparison of PXRD patterns of the compound erroneously referred to in WO 2013127971 as "letermovir sodium trihydrate" (below) (cf.

The structure of the obtained letermovir sodium mixed ethanol solvate corresponds to the structure of the compound obtained in Example 2 of WO 2013127971 (the compound erroneously referred to in WO 2013127971 as "letermovir sodium trihydrate"). The comparison of the PXRD patterns is provided in FIG. 9.

Example 11: Characterization of Sodium (S)-{8-fluoro-2-[4-(3-methoxyphenyl)-piperazine-1-yl]-3-[2-methoxy-5-(trifluoromethyl)phenyl]-3,4-dihydro-quinazoline-4-yl}acetate monohydrate The sodium (S)-{8-fluoro-2-[4-(3-methoxyphenyl)piperazine-1-yl]-3-[2-methoxy (trifluoromethyl)phenyl]-3,4-dihydroquinazoline-4-yl}acetate monohydrate obtained from examples 07 and 08 were analyzed using X-Ray Diffraction, NMR spectroscopy, Thermal gravimetric analysis, Differential scanning calorimetry and dynamic vapor sorption. The results are summarized in the table below.

Figure 2:
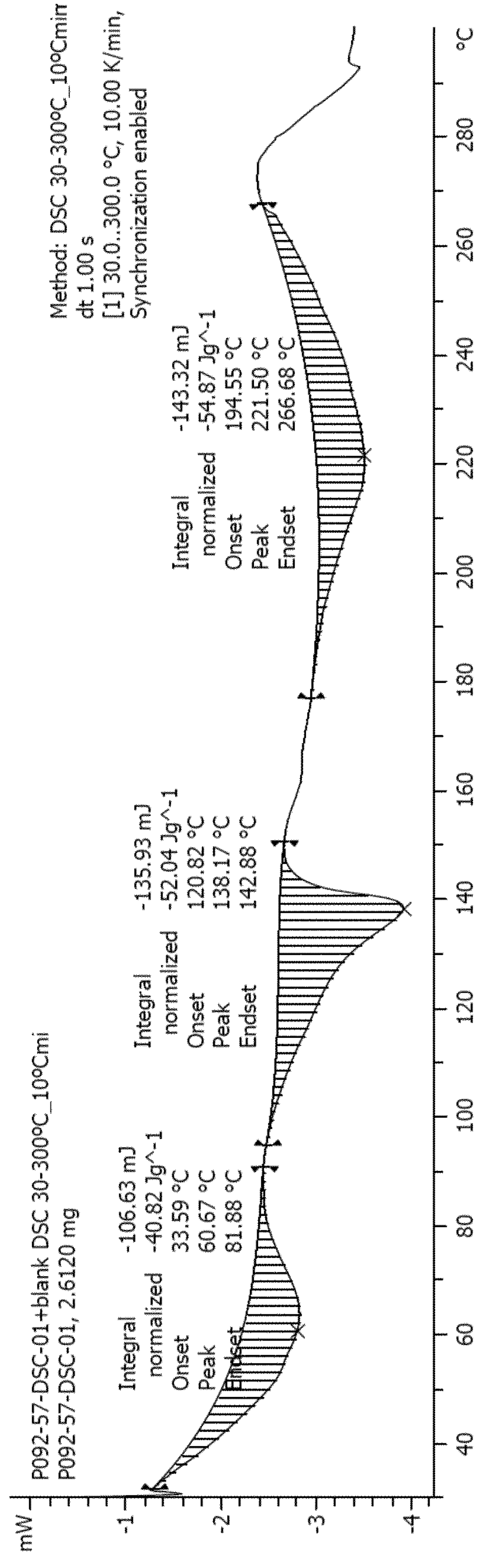
FIG. 2 shows a differential scanning calorimetric study of Form B of letermovir sodium monohydrate.
Figure 3:
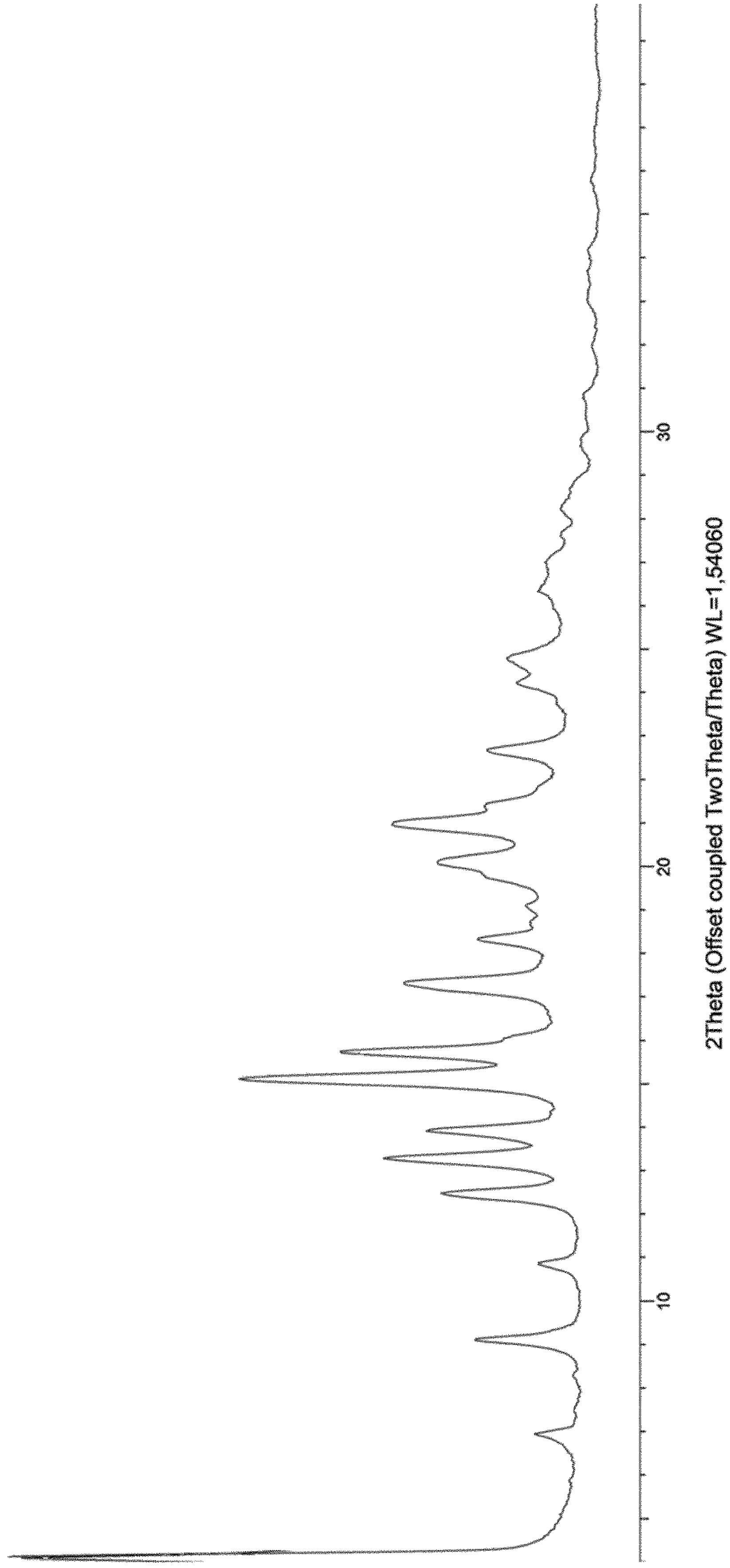
FIG. 3 shows a powder X-ray diffraction pattern (PXPD) of Form B of letermovir sodium monohydrate.

| Analysis | Results |
|---|---|
| Powder X-Ray Diffraction | Crystalline phase, medium crystallinity - FIG. 3 |
| $^{1}$H-NMR Spectroscopy | Solvent signal: water - FIG. 4 |
| Thermal Analyses | DSC: FIG. 2<br>Endothermic peak with onsets at 33.6° C. (−40.8 J/g)<br>Endothermic peak with onsets at 120.8° C. (−52.0 J/g)<br>Endothermic peak with onsets at 194.6° C. (−54.9 J/g)<br>TGA: FIG. 1<br>Weight loss of 2.5% between 40 and 100° C.<br>Weight loss of 2.5% between 100 to 160° C.<br>Weight loss due to decomposition starts at ca. 240° C. |
| Stability Experiments | Heating (vacuum oven)<br>40° C., 2-3 mbar, 15 h: No changes, possible increase in crystallinity.<br>50° C., 2-3 mbar, 60 h: No changes<br>Ageing (humidity chamber)<br>25° C./60% RH, 72 hours: minor changes<br>30° C./75% RH, 48 hours: amorphous pattern<br>Ageing (ambient conditions, closed vial)<br>No significant changes after 4 weeks. |
| Dynamic Vapor Sorption | >9.5% weight increase from 10 to 80% RH<br>>8% weight increase from 80 to 90% RH |

RH: Relative humidity

Figure 7:
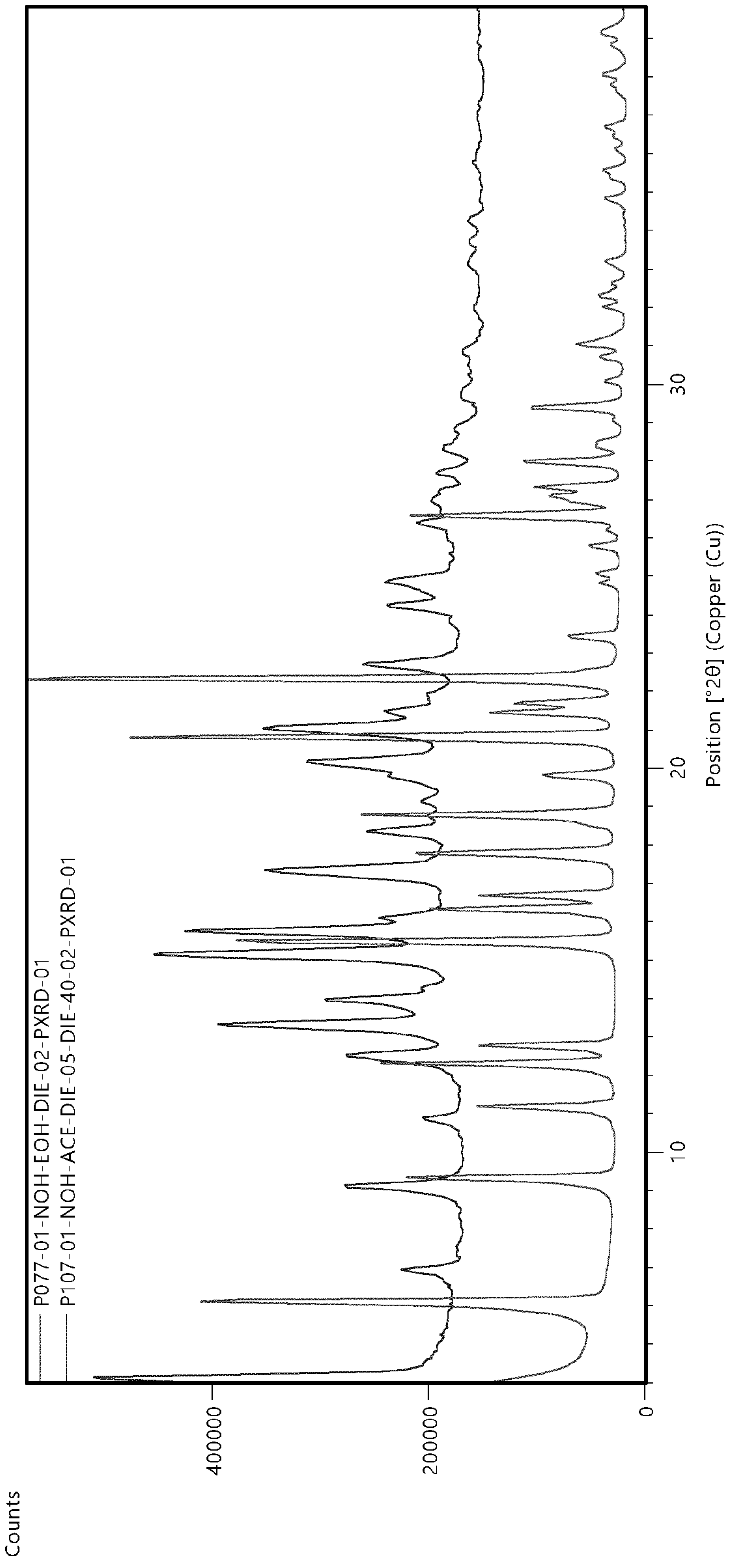
FIG. 7 shows a comparison of PXRD patterns of letermovir sodium monohydrate (above) and letermovir sodium mixed solvate (below).
Figure 8:
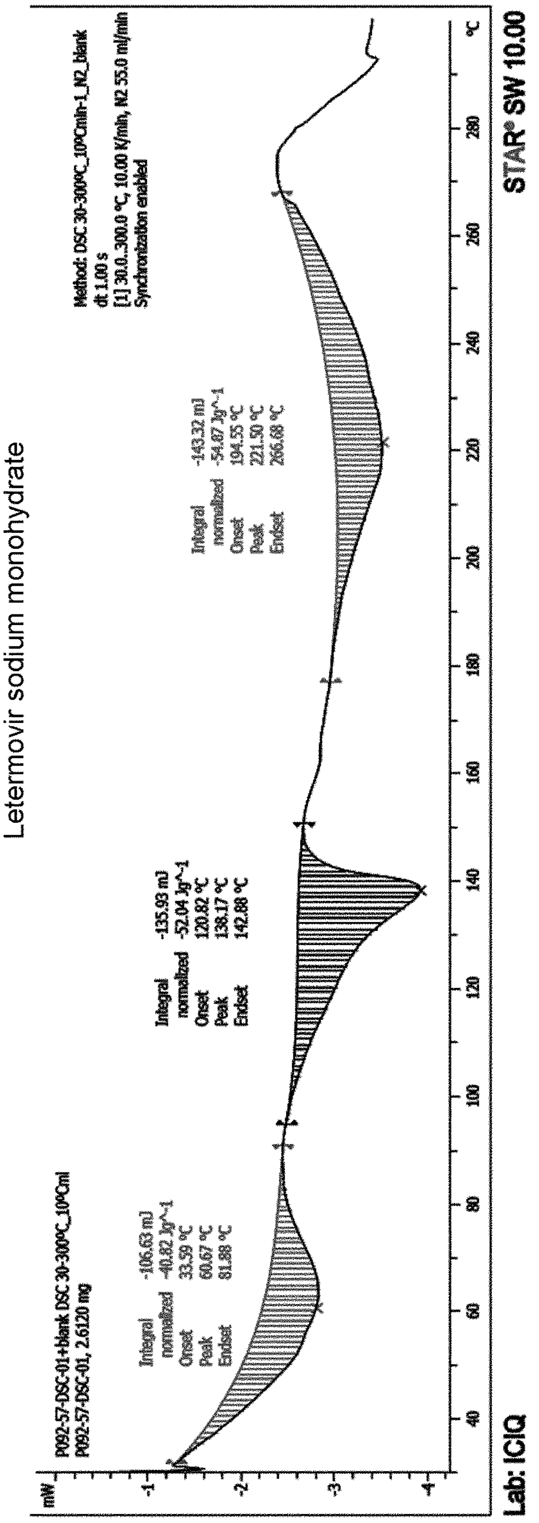
FIG. 8 shows a comparison of DSC peaks of letermovir sodium monohydrate and letermovir sodium mixed solvate.
Figure 8:
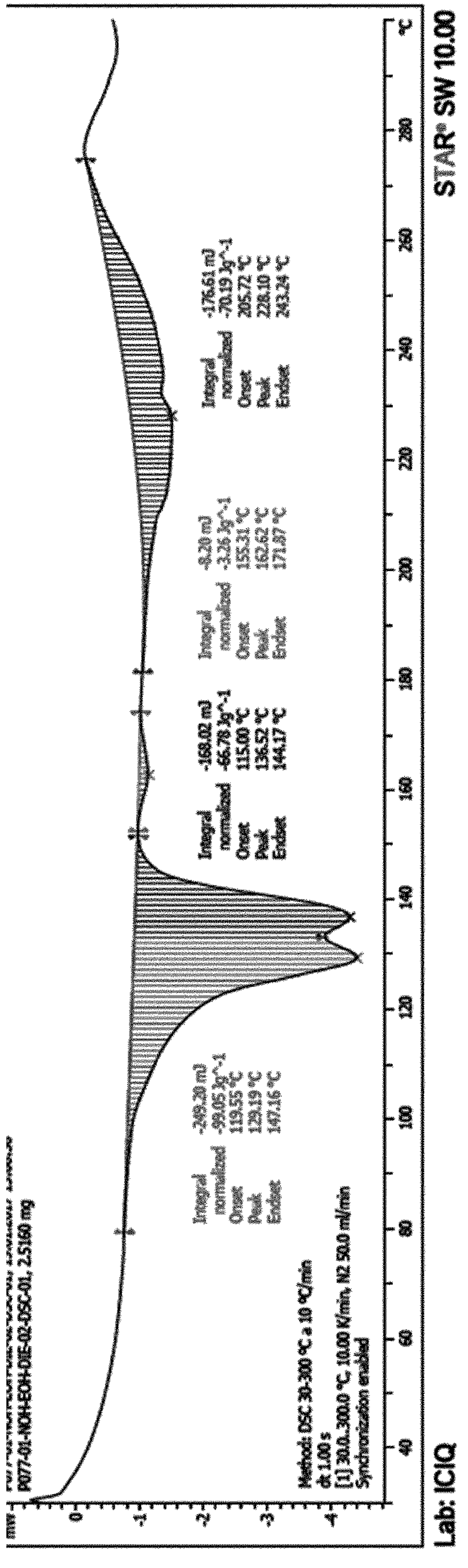

The PXRD pattern and the DSC profile of sodium letermovir monohydrate is clearly distinguishable from that of letermovir sodium mixed solvate (FIGS. 7-8).

The water content of sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate monohydrate was determined by Karl-Fischer analysis to 3.1%, which is in agreement with the theoretical water content of a monohydrate (1 molecule of water corresponds to 2.9 wt %).

No other residual solvent signals were observed in the NMR spectrum.

The stability experiments revealed that the crystalline solid is stable for over 4 weeks at ambient conditions.

Example 12: Preparation of a Crystalline Form A of Sodium (S)-{8-fluoro-2-[4-(3-methoxyphenyl) piperazine-1-yl]-3-[2-methoxy-5-(trifluoromethyl) phenyl]-3,4-dihydroquinazoline-4-yl}acetate 1 gram of amorphous sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Example 03 or 04) was dissolved in 2.5 mL methylene chloride at 40 °C and stirred for 1 hour at this temperature. Afterwards, the solution was cooled down and the solvent was evaporated at room temperature. The title compound was obtained nearly quantitatively as a white solid.

Example 13: Alternative Preparation of a Crystalline Form A of Sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate 1 gram of crystalline sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (prepared according to a procedure described in Example 01 or 02) was dissolved in 2 mL methylene chloride at 35 °C-40 °C and stirred for 1 hour at this temperature. Afterwards, the solution was cooled down and the solvent was evaporated at room temperature. The title compound was obtained nearly quantitatively as a white solid.

Example 14: Characterization of the Crystalline Form A of Sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate The polymorphic Form A of sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate monohydrate obtained from examples 10 and 11 were analyzed using X-Ray Diffraction, Thermal gravimetric analysis and Differential scanning calorimetry. The results are summarized in the table below.

Figure 5:
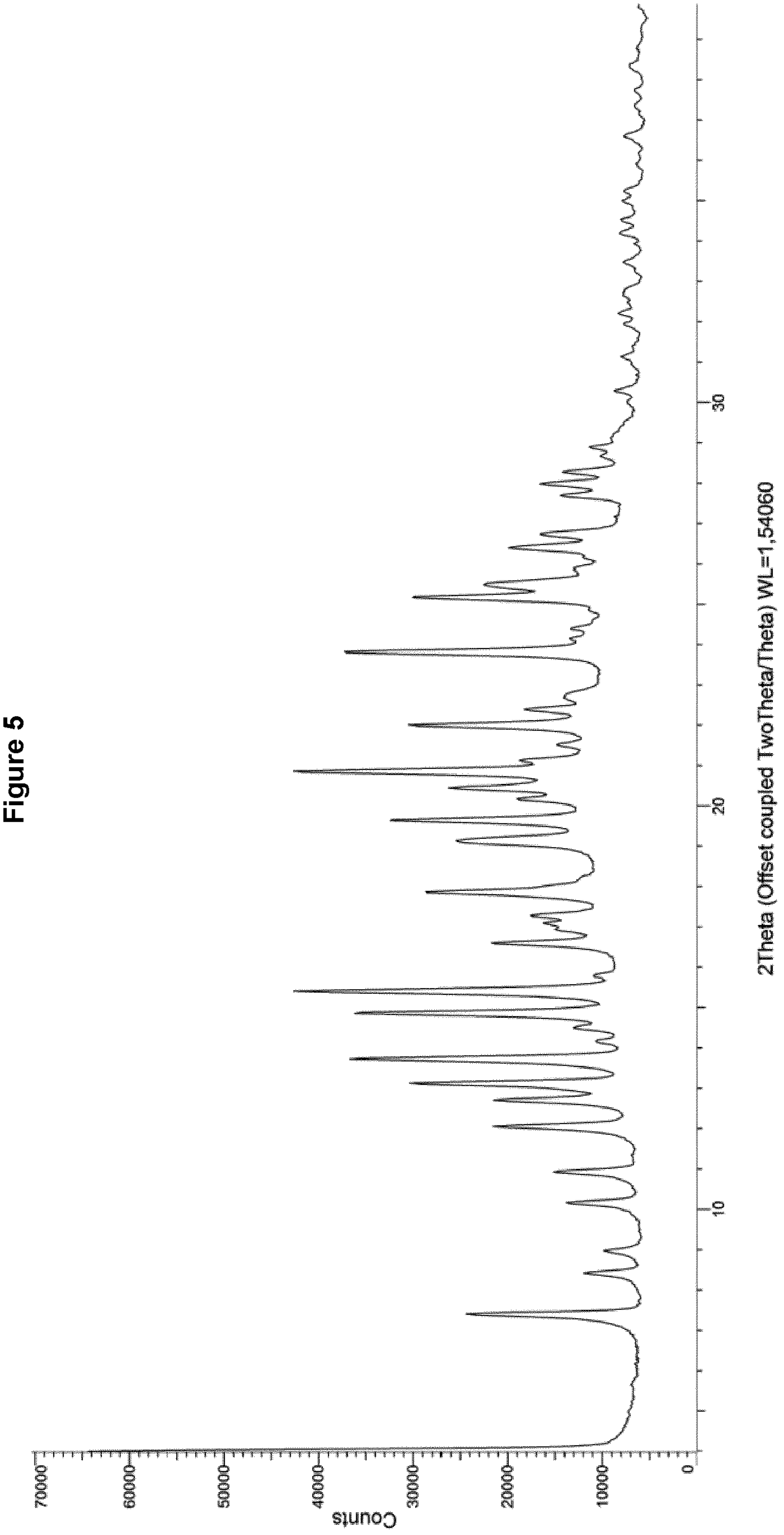
FIG. 5 shows a powder X-ray diffraction pattern (PXPD) of crystalline Form A of letermovir sodium.

| Analysis | Results |
|---|---|
| Powder X-Ray Diffraction | Crystalline phase, high crystallinity. - FIG. 5 |
| Thermal Analyses | DSC: Two wide endotherms between 40-95° C. and 95-180° C.-FIG. 6B<br>TGA: Loss of 1.6% mass between 40 and 95° C. (residual solvent)-FIG. 6A<br>Loss of ca. 2.6% mass between 95 and 180° C.<br>Decomposition at ca. 250° C. |
| Stability Experiments | Ageing (Ambient conditions)<br>25° C., 30-40% RH, 24 hours: Turns into Form B<br>Ageing (humidity chamber)<br>25° C./60% RH, 24-72 hours: Turns into Form B<br>Ageing (Ambient conditions)<br>Complete transition into Form B within in 24 hours |

The stability experiments revealed that the polymorphic form is not stable under ambient conditions and transforms into the stable form described in Example 09 within hours.

Example 15: Converting the Crystalline Form A of Sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate to the More Stable Monohydrated Form (Form B)

1 gram of the crystalline form A of sodium (S)-{8-fluoro-2-[4-(3-methoxyphenyl)piperazine-1-yl]-3-[2-methoxy-5-(trifluoromethyl)phenyl]-3,4-dihydroquinazoline-4-yl}acetate (obtained from Examples 10 or 11) was heated in a vacuum drying oven at 60 °C, 2-3 mbar for 4 hours. The obtained solid was identical by means of PXRD, TGA, DSC and NMR to the solids obtained in Examples 07 and 08.

Example 16: Preparation of a Pharmaceutical Composition in Form of an Intravenous Solution To produce a first stock solution, 1.0 g of the salt from Example 07 is dissolved in 10 ml of water for injection purposes and the salt is agitated until a clear solution is obtained. This solution is slowly added to a 20 mM phosphate buffer solution in order to produce solutions for intravenous administration with concentrations of 5 mg/ml or 10 mg/ml. The pH values of the respective solutions were at approx. pH 7.6 (5 mg/ml) and approx. pH 7.7 (10 mg/ml). Finally, the solutions obtained are sterile-filtered and filled into appropriate sterilized containers. The containers are sealed with infusion plugs and flange caps.

If necessary, the solutions produced in this way can be lyophilized for storage before the containers are sealed and they can be reconstituted at a later date in order to be used.

Example 17: Preparation of a Pharmaceutical Composition in Form of an Tablet

In order to produce a solid formulation for oral administration the salt (50%) from Example 07 is screened and mixed with calcium hydrogen phosphate dihydrate (48%), croscarmellose sodium (5%), polyvinylpyrrolidone (5%) and colloidal silica gel (1%). Then, screened magnesium stearate (1%) is added. This press mixture is then directly used to produce tablets.

Example 18: Assessment of Physiological Efficacy

The in vitro effects of the compositions according to the present invention on the replication of the HCMV (human cytomegalovirus) can be seen in the following antiviral assay:

HCMV Fluorescence-Reduction Test.

The test compositions are used as a 50-millimolar (mM) solution in dimethyl sulphoxide (DMSO). Ganciclovir®, Foscarnet® or Cidofovir® can be used as reference compositions. One day before the beginning of the test, $1.5\times10^4$ human foreskin fibroblasts (NHDF cells)/well are seeded in 200 mL of cell culture medium in Wells B2-G11 of 96-well plates (black with transparent floor). The wells along the edges of each 96-well plate are filled with 200 μL of medium only in order to prevent edge effects. On the day of the test the cell culture medium in Wells B2-G11 of each 96-well plate is vacuumed off by a suction device and replaced with 100 μL of virus suspension (multiplicity of infection (MOI): 0.1-0.2). The virus used is a recombinant HCMV which has integrated an expression cassette for green fluorescence protein (GFP) in the virus genome (HCMV AD 169 RV-HG [E. M. Borst, K. Wagner, A. Binz, B. Sodeik, and M. Messerle, 2008, J. Virol. 82:2065-2078.]). After an incubation time of 2 h at 37 °C and 5% $CO_2$, the virus inoculate is vacuumed off by a suction device and all wells, with the exception of the wells in Column 3, are filled with 200 μL of cell culture medium. Column 2 is not treated further and serves as a virus control. The wells in Column 3 are each filled with 300 μL of test substance (diluted in cell culture medium) for duplicate analysis. The concentration of the respective antiviral substance in Column 3 is about 27 times as concentrated as the respective anticipated $EC_{50}$ value. The test substance in Column 3 is diluted in 8 steps to a concentration of 1:3 across the 96-well plate by transferring 100 μL from each column into its respective right-hand column, where it is mixed with the 200 μL of cell culture medium already present there. In this way, three antiviral substances are tested in duplicate analyses. The plates are incubated for 7 days at 37 °C and 5% $CO_2$. Subsequently, all wells on the plate are washed 3 times with PBS (phosphate-buffered saline) and filled with 50 μL of PBS. The GFP intensity of each well in a 96-well plate is then determined using a fluorescence scanner (FluoBox; Bayer Technology Services GmbH; filter settings: GFP, Ex 280 nm, Em 520 nm). The measured values thus obtained can be used to determine the $EC_{50}$ of an anti-HCMV:

$EC_{50}$ (GFP-RA)=substance concentration in μM which reduces GFP fluorescence by 50% in comparison to the untreated virus control.

The invention claimed is:

1. A method of preparation of crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate of formula (I)

(I)

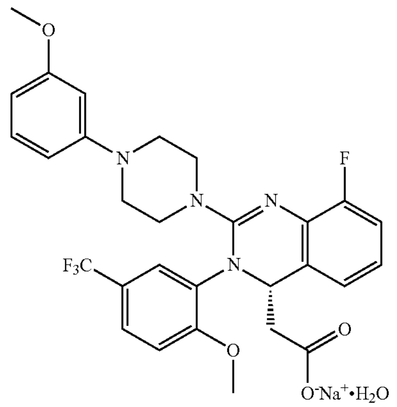

comprising the steps:

A-1) providing a suspension of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in diisopropylether, B-1) stirring the suspension obtained in step A-1 at a temperature in the range of from 40 °C to 60 °C for at least 10 hours, and C-1) removing the diisopropylether to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a crystalline solid, or, alternatively to steps A-1, B-1 and C-1:

A-2) providing a solution of sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate in methylene chloride, B-2) stirring the solution obtained in step A-2 at a temperature in the range of from 40 °C to 60 °C for at least 30 minutes; and C-2) removing the methylene chloride to obtain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as a crystalline solid.

2. The method according to claim 1, further comprising the subsequent step of heating the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate to a temperature in the range of from 40 °C to 60 °C in vacuo.

3. The method according to claim 1, comprising the steps A-1, B-1 and C-1.

4. The method according to claim 1, comprising the steps A-2, B-2, and C-2.

5. The method according to claim 3, wherein in step A-1 the solid/solvent ratio of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropyl ether is from 10 g/L to 50 g/L.

6. The method according to claim 3, wherein in step B-1 the suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropylether is stirred at a temperature in the range of from 50 °C to 55 °C for at least 10 hours.

7. The method according to claim 3, wherein in step C-1 the diisopropylether is removed by filtration.

8. The method according to claim 3, further comprising the subsequent step of drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 20 °C to 60 °C in vacuo.

9. The method according to claim 4, wherein in step A-2 the concentration of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate is from 0.5 M to 2 M.

10. The method according to claim 4, wherein in step B-2 the solution of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in methylene chloride is stirred at a temperature in the range of from 40 °C to 60 °C for at least 1 hour and then cooled down to room temperature.

11. The method according to claim 4, wherein in step C-2 the methylene chloride is removed by evaporation.

12. The method according to claim 4, further comprising the subsequent step of drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 30 °C to 60 °C in vacuo.

13. A crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate of formula (I)

(I)

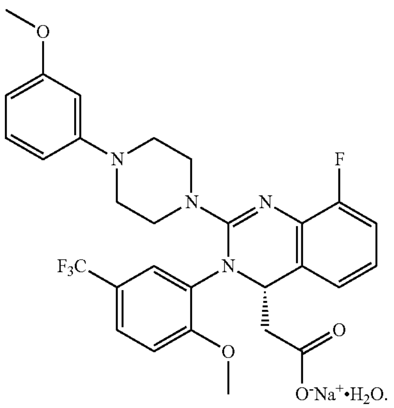

14. The crystalline sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate monohydrate according to claim 13, having an X-ray diffraction pattern which comprises 2-theta angle values of: 7.0, 9.1, 10.9, 13.3, 14.0, 15.2, 17.4, 18.4, 24.3 degrees, and said 2-theta angle values have a normal deviation of +0.1°.

15. The crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate obtainable by the method as defined in claim 1.

16. A pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as defined in claim 13 and at least one pharmaceutically acceptable carrier, excipient and/or diluent.

17. A method for treatment of a virus infection by a member of the herpes viridae group, comprising administering to an infected subject a pharmaceutical composition as defined in claim 16.

18. A method for treatment of a virus infection by a member of the herpes viridae group comprising administering to an infected subject the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate monohydrate as defined in claim 13.

19. The method according to claim 3, wherein in step B-1 the suspension of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate in diisopropylether is stirred at a temperature in the range of from 50 °C to 55 °C for 12 to 18 hours.

20. The method according to claim 3, further comprising the subsequent step of drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 20 °C to 60 °C in vacuo for 4 hours or more.

21. The method according to claim 4, wherein in step B-2 the solution of sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate in methylene chloride is stirred at a temperature in the range of from 45 °C to 55 °C for at least 1 hour and then cooled down to room temperature.

22. The method according to claim 4, further comprising the subsequent step of drying the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate at a temperature in the range of from 30 °C to 60 °C in vacuo for 4 hours or more.

23. A method for treatment of a human cytomegalovirus (HCMV) infection comprising administering to an infected subject a pharmaceutical composition as defined in claim 16.

24. A method for treatment of a human cytomegalovirus (HCMV) infection comprising administering to an infected subject the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as defined in claim 13.

25. A method for prevention of a human cytomegalovirus (HCMV) infection comprising administering to a subject a pharmaceutical composition as defined in claim 16.

26. A method for prevention of a human cytomegalovirus (HCMV) infection comprising administering to a subject the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate monohydrate as defined in claim 13.

* * * * *